US007220574B2

(12) United States Patent
Rupp et al.

(10) Patent No.: US 7,220,574 B2
(45) Date of Patent: May 22, 2007

(54) **HYPHEN-SPECIFIC FACTORS FROM *CANDIDA ALBICANS***

(75) Inventors: Steffen Rupp, Stuttgart (DE); Franz-Josef Johannes, Leonberg (DE); Kai Sohn, Schwäbisch-Gmünd (DE)

(73) Assignee: Fraunhafer-Gasellschaft zur Forderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 10/275,933

(22) PCT Filed: May 10, 2001

(86) PCT No.: PCT/EP01/05363

§ 371 (c)(1),
(2), (4) Date: Jul. 2, 2003

(87) PCT Pub. No.: WO01/85989

PCT Pub. Date: Nov. 15, 2001

(65) Prior Publication Data

US 2004/0014061 A1 Jan. 22, 2004

(30) Foreign Application Priority Data

May 11, 2000 (DE) ............................... 100 23 130

(51) Int. Cl.
*C12M 1/36* (2006.01)
*C12P 19/34* (2006.01)
*C12Q 1/68* (2006.01)
*C07H 21/04* (2006.01)
*G01N 33/48* (2006.01)

(52) U.S. Cl. ...................... 435/287.2; 435/6; 435/91.2; 536/24.3; 977/792

(58) Field of Classification Search .................. 435/6, 435/320.1; 536/23.1, 24.3
See application file for complete search history.

(56) References Cited

U.S. PATENT DOCUMENTS 5,776,694 A 7/1998 Sheiness et al.
6,747,137 B1 * 6/2004 Weinstock et al. ......... 536/23.1

FOREIGN PATENT DOCUMENTS

| EP | 1 026 259 A1 | 8/2000 |
| EP | 1 077 264 A2 | 2/2001 |
| EP | 1 094 120 A2 | 4/2001 |
| WO | WO 97/31256 | 8/1997 |
| WO | WO 98/18927 | 5/1998 |
| WO | WO 99/39210 | 8/1999 |
| WO | WO 99/40434 | 8/1999 |

OTHER PUBLICATIONS

William A. Fonzi and Michael Y. Irwin, Isogenic Strain Construction and Gene Mapping in *Candida albicans*, Genetics, 1993, vol. 134, p. 717-728.
Hsiu-Jung Lo et al., Nonfilamentous *C. albicans* Mutants Are Avirulnet, Cell, 1997, vol. 90 p. 939-949.
DATABASE EBI 'Online!, EMBL; Jun. 20, 1997, Choi, S.Y.: "*Candida* sp. HN95 CIP1-Gene" retrieved from EBI, accession No. Y13973, Database accession No. Y13973 Database accession No. Y13973 XP002231416 das ganze Document.
DATABASE TEMBL 'Online! EMBL; Jul. 1, 1997, Hong, Y. et al.: "Cadmium induced CIP1 protein" retrieved from EMBL, accession No. P87221 Database accession No. P87221 XP002231417 das ganze Document.
DATABASE EBI 'Online! EMBL; May 11, 1994 Rasmussen, S. et al.: "*S. cerevisiae* chromosome XI readingframe ORF YKL067w" Database accession No. Z28076 Database accession No. Z28076 XP002231418 das ganze Document.
DATABASE TREMBL 'Online! EMBL; Jun. 1, 1994 Rasmussen, S.W.: "Nucleoside Diphosphate Kinase (EC 2.7.4.6.)" retrieved from EMBL, accession No. P36010 Database accession No. P36010 XP002231419, das ganze Document.
DATABASE TREMBL 'Online! EMBL; Apr. 14, 1995, Budde, E. et al. *Saccharomyces cereviseae*, hydroperoxide resistance (HYR1) gene, complete cds retrieved from EMBL, accession No. U22446 Database accession No. U22446 XP002231420 das ganze Document.
DATABASE TREMBL 'Online! EMBL; Jan. 1, 1990, Schwelberger, H.G. et al.: "Fructose-bisphosphate aldolase" retrieved from EMBL, accession No. P14540 Database accession No. P14540, XP002231421, das ganze Document.
Database EBI 'Online! EMBL; Mar. 1991, Schwelberger, H.G. et al.: "Yeast FBA1 gene for fructose-biphosphate aldolase" retrieved from EMBL, accession No. X15003 Database accession No. X15003, XP002231422, das ganze Document.
Paravicini Gerhard et al.: "The *Candida albicans* PKC1 gene encodes a protein kinase C homolog necessary for cellular integrity but not dimorphism." YEAST, Bd. 12. Nov. 8, 1996, Seiten 741-756, XP008013926, ISSN: 0749-503X. das ganze Document.
Database Trembl (online) EBI; Jul. 1, 1997; Hong, Y., et al.; "Cadmium induced CIP1 protein".
Database Trembl (online) EBI; Jan. 1, 1990; H. G. Schwelberger, et al.; "Fructose-biphosphate aldolase".

* cited by examiner

*Primary Examiner*—Shubo (Joe) Zhou
(74) *Attorney, Agent, or Firm*—Bateman IP Law Group

(57) ABSTRACT

The present invention relates to biochips, in particular nucleotide chips, which contain hyphen-specific proteins coding nucleotides, protein chips which contain hyphen-specific proteins, and antibody chips which contain antibodies directed against these hyphen-specific proteins, diagnostic compositions which contain these nucleotide, protein, or antibody chips, processes for the location and identification of substances which are therapeutically effective against diseases caused by types of *Candida* and processes for the diagnosis of a disease caused by *Candida*.

4 Claims, 4 Drawing Sheets a)

Can34 (Δefg1/Δcph1)

Sc5314

Differential proteome analyses, Culture medium α-MEM b) Northern blott

HYPHEN-SPECIFIC FACTORS FROM *CANDIDA ALBICANS*

The present application is a nationalization of PCT Application No. PCT/EP01/05363, filed May 10, 2001, claiming priority to German Patent Application 10023130.6, filed May 11, 2000.

BACKGROUND

The present invention relates to biochips, in particular nucleotide chips, which contain nucleotide sequences coding hyphen-specific proteins, protein chips, which contain hyphen-specific proteins, and antibody chips, which contain antibodies directed against these hyphen-specific proteins, diagnostic compositions which contain these nucleotide, protein, or antibody chips, processes for the location and identification of substances, which are therapeutically effective against diseases caused by types of *Candida* and processes for the diagnosis of a disease caused by *Candida*.

Along with the yeasts of the Saccharomycetaceae family, which have been used commercially, e.g. in the food industry, for a long time, asporogenous yeasts such as, for example, yeasts of the genus *Candida*, also number among the budding funguses or yeasts. Several members of the genus *Candida* are able to form mycel aggregates. Others reproduce only by sprouting. *Candida albicans* is the most frequently isolated human pathogenic fungus. *Candida albicans* frequently causes opportunistic infections, i.e. infections in immunosuppressed patients by normally relatively unproblematic microbes. Infections of this type take a serious course in these patients and decisively shorten the survival time, for example, of HIV-infected patients or of cancer patients treated with chemotherapy or radiation therapy. Presently, the treatment of systemic infections with *Candida albicans* is carried out principally by means of azoles or polyenes. However, the treatment by means of these two classes of substances has disadvantages. Polyenes lead to strong side effects while resistance to the azoles is increasingly developing (DiDomenico, 1999, *Curr Opin Microbiol* 2, 509 to 515, Georgopapadakou, 1998, *Curr Opin Microbiol* 1, 547 to 557).

Since the clinical findings of fungus infections are predominantly uncharacteristic, forming the exact diagnosis of fungal infections, in particular of *Candida* infections, is extremely difficult. Where a *Candida* attack on the skin or the mucus membranes is suspected, for example, surface smears must be taken and examined microscopically. In attacks on internal organs, organ biopsies must be examined histologically in order to detect invasive growth. For the diagnosis of a generalized *Candida* infection, a specular examination of the ocular fundus is indicated. Furthermore, several blood cultures, which must be taken venously on successive days, must be examined. In case the kidneys are involved the urine must be examined in addition. Microscopic native preparations of this kind permit, however, only the detection of polymorphic fungal cells (hyphens, pseudohyphens, and blastospores) and spores, indeed without enabling the exact species to be determined and specific therapeutic measures to be introduced.

Along with the microscopic detection, it is therefore indispensable to establish cultures for the determination of the exact species. A further diagnostic possibility, which nevertheless Up to now has not had the desired informational value, is the detection of *Candida* antigens in the serum of the patient. Although a high titer indeed argues for a systemic *Candida* infection, it still does not prove it, while a negative finding cannot rule out a systemic infection.

The development of further improved diagnostics for doubt-free assignment of a disturbance of health to the infections caused by representatives of the *Candida* family and of antimycotics for the treatment of infections caused by representatives of the *Candida* family is therefore urgently needed.

SUMMARY OF THE INVENTION

The technical problem underlying the present invention therefore consists of providing for the means and processes for the diagnosis of infections caused by *Candida albicans* and for the development of substances, which are therapeutically effective against diseases caused by *Candida*. The invention solves the technical problem underlying it through the preparation of biochips, in particular, of a nucleotide chip, including a solid substrate and at least one nucleotide sequence fixed on it which is suitable for the identification and transcription of a gene coding for a hyphen-specific protein from *Candida*, in particular *Candida albicans*, where this nucleotide sequence is selected from the group consisting of:
(a) a nucleotide sequence, defined in SEQ ID no. 1, 2, 3, 4, 12, 13, 15 or 17, or a complementary strand or portion thereof,
(b) a nucleotide sequence, coding an amino acid sequence, defined in SEQ ID no. 5, 6, 7, 8, 14, 16 or 18, or a complementary strand or part thereof, and
(c) a nucleotide sequence, which hybridizes with one of the nucleotide sequences named in (a) or (b).

BRIEF DESCRIPTION OF THE DRAWINGS

The invention will now be described, in association with the drawings, in which.

Figure 1:
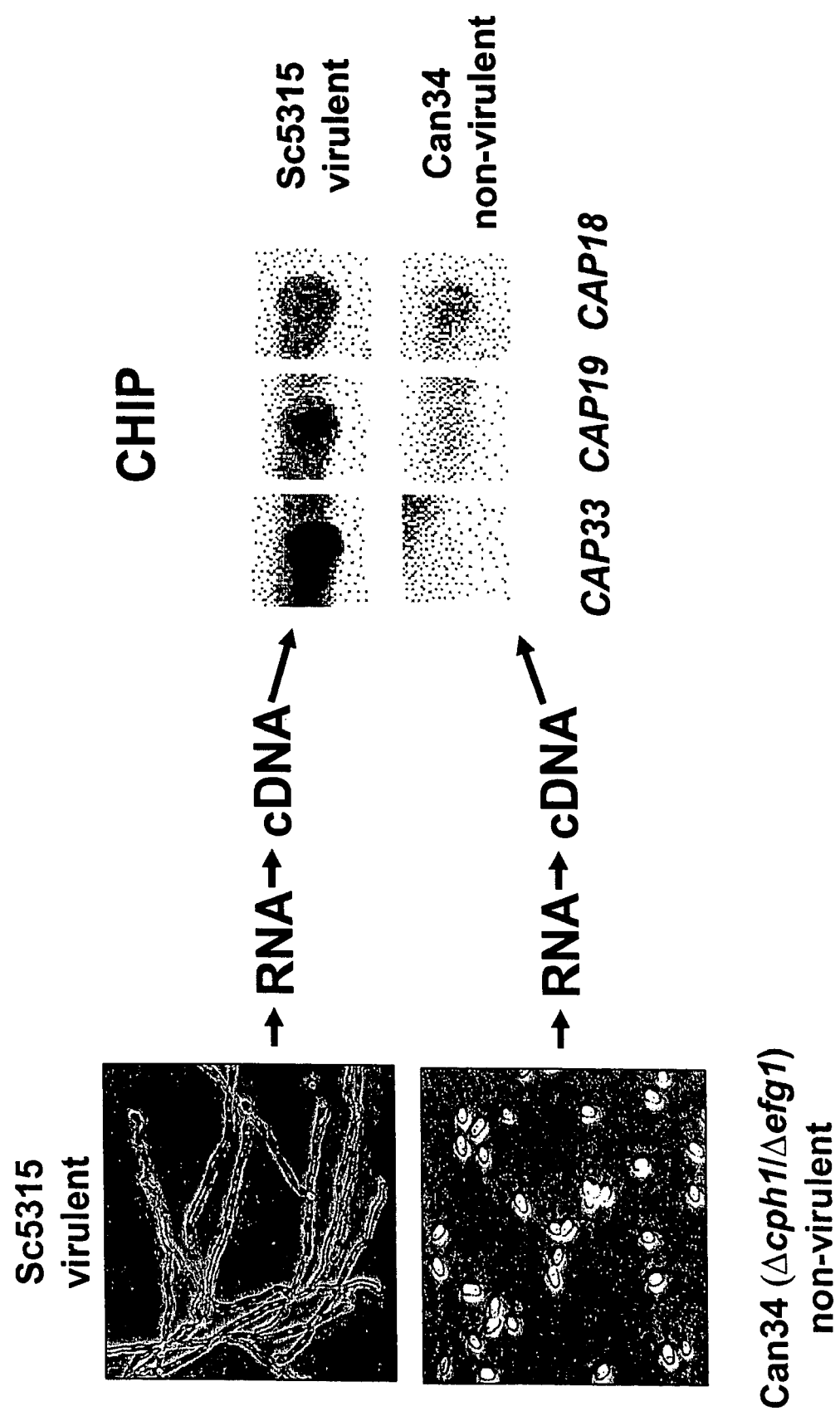
FIG. 1 shows microscopic pictures of the virulent, hyphally growing *Candida albicans* strain Sc5315 and the non-virulent *Candida* strain Can34 (Δcph1Δefg1) growing in the manner of a yeast.

In connection with the present invention, it is understood that a biochip means a device which contains, in immobilized or fixed form, a plurality of biological substances—by way of example, nucleotide sequences, proteins or antibodies—and, with whose aid, a small quantity of a ligand, which under suitable circumstances can bind to the biological substance, can be detected in a small sample by means of hybridization and/or binding methods. It is understood that a nucleotide chip means a device which contains a plurality of different nucleic acids or nucleotide sequences such as DNA or RNA in immobilized form, and with whose aid a small amount of a complementary nucleic acid in a small sample liquid or—by means of DNA/protein binding tests—a small amount of a protein binding to nucleic acids can be detected.

According to the invention, the nucleotide chips contain, fixed on a solid substrate, nucleotide sequences, which exclusively code proteins, which are expressed in the hyphally growing form of *Candida albicans* or which exclusively regulate the expression of hyphen-specific proteins. That is, the nucleotide sequences contained on the nucleotide chips according to the invention are not expressed during the yeast-like growth of *Candida*. The nucleotide sequences described according to the invention and the proteins coded by them have no significant homologies to a related, non-pathogenic, non-hyphally growing fungus, for example with proteins of *Saccharomyces cerevisiae*. It is known that the filamentous growth, that is the formation of hyphae, is an important prerequisite for the occurrence of the virulent qualities of *Candida* (Mitchell, 1998, *Curr. Opin. Microbiol.*, 1, 687–692). Thus, forms of *Candida albicans*, which form no hyphae, are non-virulent in a model system (*Mus musculus*) (Lo et al., 1997, *Cell* 90, 939 to 949). Thus, in connection with the present invention, it is understood that a hyphen-specific protein means a protein and/or peptide which is expressed exclusively in the types of the genus *Candida* and preferably has significance for the virulence of *Candida*, in particular *Candida albicans*.

The nucleotide sequences used according to the invention, occurring specifically in the pathogenic form of *Candida albicans* and the proteins coded by these, thus represent outstanding diagnostic auxiliary means for the recognition of local or systematic candidoses, in particular for the recognition of local or systemic *Candida albicans* infections. Moreover, they offer the possibility, in the case of a *Candida* infection, of distinguishing hyphally growing, therefore virulent, *Candida albicans* forms from yeast-like growing, therefore non-virulent, forms of *Candida albicans*.

Moreover, the nucleotide sequences and proteins used according to the invention prove to be particularly valuable for the development of medicaments for fighting candidoses. The nucleotide sequences and proteins according to the invention can be used as targets for the identification specifically of substances effective against these. Thus, substance libraries can be searched for the interaction of substances present in them with proteins according to the invention or nucleotide sequences according to the invention.

The invention thus relates in its preferred form of embodiment to an aforementioned nucleotide chip, which includes a nucleotide sequence, which is a protein-coding nucleotide sequence, selected from the group consisting of the nucleotide sequences of SEQ ID No. 1, 2, 3, 4, 13, 15, and 17. These nucleotide sequences code the amino acid sequences described in SEQ ID No. 5, 6, 7, 8, 14, 16, and 18. These sequences are particularly helpful in the diagnosis of diseases, which are caused by types of *Candida*, in that they enable the selective detection of the presence of *Candida* in surface smears or organ biopsies. For example, the nucleotide sequences according to the invention contained on such a nucleotide chip can be hybridized with marked DNA samples, which are isolated from sources such as skin smears, biopsy samples, or specially established fungal cultures, or amplified by means of PCR methods under stringent conditions. Since the nucleotide sequences according to the invention have no significant homologies to nucleotide sequences from related funguses, the detection of a hybridization thus permits the detection of *Candida* in a sample infected with fungus. The nucleotide sequences used according to the invention, however, make possible not only the simple detection of *Candida*, but also the detection that *Candida* is growing in hyphalic form and has the correspondingly virulent properties. For example, mRNA can be selectively isolated from skin swabs or biopsy samples and/or amplified by means of PCR methods. After marking with suitable marking materials, the mRNA so obtained is hybridized with the nucleotide chip containing the nucleotide sequences according to the invention. Since the nucleotide sequences according to the invention are expressed and transcribed exclusively during the hyphalic growth of *Candida*, not during the yeast-like growth, the detection of a hybridization permits, with the use of isolated mRNA, the detection that *Candida* is found in the transition to the hyphalic, and thus virulent, growth phase.

In an additional preferred form of embodiment, the invention relates to the aforementioned nucleotide chip, which contains nucleotide sequences which are regulator elements of hyphen-specific *Candida* protein-coding genes, therefore, elements, which in particular make possible the transcription of the protein-coding regions functionally connected with these regulatory elements, for example promoters, transcription termination signals, silencers, enhancers, and so on. These particularly preferred nucleotide sequences can in particular be promoters, particularly preferably the promoter represented in SEQ ID No. 12. The regulatory elements according to the invention, in particular promoters, particularly preferably the promoter described in SEQ ID). No. 12, prove to be particularly advantageous to the extent that they include the regulation sequences necessary for the induction of hyphen-specifically expressed proteins and accordingly can be used in order to identify additional specific *Candida* proteins which, through binding to these regulatory elements, can induce or inhibit in vivo the transcription of hyphen-specific proteins, in particular of proteins with the amino acid sequences described in SEQ ID No. 5, 6, 7, 8, 14, 16, and 18. After the identification of such proteins, nucleotide chips, which contain the regulatory elements of hyphen-specifically expressed protein-coding nucleotide sequences can be used to identify substances of any kind, which inhibit the interaction between the regulatory elements and the proteins binding thereto. With the use of nucleotide chips of this type it is therefore possible to identify substances, which inhibit the expression of hyphen-specific proteins and that thus can potentially be used as medicaments acting specifically against *Candida* infections.

The invention relates, in a further particularly preferred form of embodiment, to the aforementioned nucleotide chip, which has DNA, RNA, or PNA sequences as nucleotide sequence. PNA (peptide nucleic acid, or polyamide nucleic acid) sequences are molecules, which are not negatively charged and act in a manner similar to DNA (Nielsen et al., 1991, *Science*, 254, 1497–1500; Nielsen et al., 1997, *Biochemistry*, 36, 5072–5077; Weiler et al., 1997, *Nuc. Acids Res.*, 25, 2792–2799). PNA sequences include a polyamide backbone of N-(2-aminoethyl)-glycine units, and have no glucose units and no phosphate groups.

According to the invention, the nucleic acid molecules, which can be fixed on a substrate, can be isolated from natural sources, preferably from *Candida albicans*. For example, the nucleic acid molecules can be isolated and amplified by means of PCR methods, whereby double-stranded molecules are obtained. According to the invention, the nucleic acid molecules can, however, also be synthesized in vitro according to known processes, whereby single-stranded oligonucleotides or peptide-oligonucleotides are obtained. Through the choice of a suitable primer, desired regions of the nucleic acids, according to the invention, i.e. individual regions as well as the whole reading frame of the gene, can be isolated and amplified. By means of current molecular biological techniques it is possible to introduce mutations of various kinds into the nucleic acid molecules, according to the invention. Thereby, for example, sequence variants can be realized, which appear in different clinical *Candida* isolates. These types of mutations realized by the invention can be insertions, deletions, duplications, inversions, additions, exchanges or the like, even of unusual nucleotides. In this way, however, it is also possible to produce modified oligonucleotides with functional groups, which make possible a covalent binding of the oligonucleotide to the substrate material for the production of the nucleotide chips according to the invention. Thus, for example, oligonucleotides with amino modifications or biotin groups can be produced, which can bind covalently to chemically reactive groups (epoxides) contained on the surface of the substrate material or to streptavidin groups or derivatives thereof. In a further preferred form of embodiment of the invention, it is provided that nucleic acids are provided with nucleoside derivatives containing photosensitive protective groups.

According to the invention, nucleotide sequences can also be used for the nucleotide chip, which are produced by fusion of the nucleotide sequences according to the invention with genes or segments of genes from other sources. According to the invention, shortened nucleotide sequences of the aforementioned type can also be used, to the extent that they have said hyphen specificity. According to the invention, it is provided that shortened nucleotide sequences have a length of at least 15 base pairs.

In an additional form of embodiment of the invention, it is provided that the nucleotide chip also contains nucleotide sequences of the aforementioned type, which according to the invention, hybridize with the aforementioned nucleotide sequences. Hybridization in connection with this aspect of the invention means hybridization under conventional hybridization requirements, as they are described in Sambrook et al. (*Molecular Cloning. A Laboratory Manual.* Cold Spring Harbor Laboratory Press, 2nd edition 1989), preferably under stringent requirements. According to the present invention, one speaks of a hybridization if after washing for an hour with 1×SSC and 0.1% SDS at 55° C., preferably at 62° C., and particularly preferably at 68° C., in particular for one hour [with] 0.2×SSC and 0.1% SDS at 55° C., preferably at 62° C., and particularly preferably at 68° C., a positive hybridization signal is still observed. According to the invention, a nucleotide sequence hybridizing with one of the nucleotide sequences specified in the sequence protocols can, under washing conditions of this type, be used, by immobilization on the solid substrate, for the nucleotide chip, according to the invention.

The identification and isolation of hybridizing nucleotide sequences can be done, by way of example, with the use of one of the nucleotide chips, according to the invention, said nucleotide chip containing the aforementioned nucleotide sequences or parts of these molecules or their complementary strands. The nucleotide chip used for the identification and isolation of hybridizing nucleotide sequences can contain, by way of example, nucleotide sequences which have exactly or essentially the nucleotide sequences represented under SEQ ID No. 1 to 4, 12, 13, 15 or 17, or parts of these sequences or complementary strands. However, the nucleotide chip can also contain synthetic fragments, which have been produced with the aid of the usual synthesis techniques and whose sequence, according to the invention, agrees essentially with one of the nucleotide sequences. In this way, nucleotide sequences from clinical *Candida* isolates, according to the invention, can be isolated and be made available for the nucleotide chip, which contain deviations or mutations with respect to the nucleotide sequences described in SEQ ID No. 1 to 4, 9 to 13, 15 or 17.

According to the invention, the molecules hybridizing with the nucleotide sequences also include fragments, derivatives, functional equivalents and/or allelic variants of the above-described nucleotide sequences, which code a protein according to the invention or guarantee its hyphen-specific expression. In the statement above "fragments" are understood to mean parts of the nucleotide sequences, which are long enough in order to code the hyphen-specifically expressed protein or to assure hyphen specificity. The expression "derivative," "functional equivalent," or "mutant deviation" means in connection with the present invention that the sequences of these molecules differ from the sequences of the above-described nucleotide sequences in one or more positions, but have a high degree of homology to these sequences at the nucleotide level. Homology here means a sequence identity of at least 40%, in particular an identity of at least 60%, preferably over 80% and particularly preferably over 90%, 95%, 97% or 99% at the nucleic acid level.

According to the invention, the nucleotide chips contain nucleotide sequences fixed or immobilized on a solid substrate. In connection with the present invention, the term "solid substrate" means an insoluble matrix. In the preferred form of embodiment, the solid substrate consists of a hydrophobic or weakly hydrophilic material like transparent glass, silica dioxide, metal oxides, polymers and copolymers of dextrans or amides, by way of example, acryl amide derivatives, cellulose, nylon, or polymeric materials such as polyethylene terephthalate, cellulose acetate, polystyrene or polymethylmethacrylate, or a polycarbonate of bisphenol A. Before fixing the nucleotide sequences, the substrate material is preferably pretreated with a surface-activating agent such as poly-L-lysine, polyethylenimine, or polyalkylamine in order to improve the fixing of the nucleotide sequences on the substrate material. In another form of embodiment, glass used as substrate is pretreated with a silane-coupling agent, which has an amino group, an aldehyde group, or an epoxy group. However, the commercially available precoated types of substrate such as poly-L-lysine (Sigma Diagnostics), Super-Aldehyde (Telechem), Super-Amine (Telechem), Silane Prep (Sigma), CMT GAPS (Corning), Type I (Clontech), Type II (Clontech), Arraylink (GeneScan Europe), Type I (Eppendorf), Type II (Eppendorf), Epoxysilan (Quantifoil) and Cast/FastSlides (Schleicher & Schüll) can also be used for the nucleotide chip according to the invention. Other suitable substrates are those that are used for photolithographically produced nucleotide chips, for example, those described in Lipshutz et al. (Lipshutz, Fodor, Gingeras and Lockhart, 1999, *Nat. Genet.*, 21, 20–24). In a particularly preferred form of embodiment, substrates are used which have a coating of poly-L-lysine, as described in DeRisi et al. (DeRisi, J. L., Iyer, V. R., and Brown, P. O., 1997, *Science,* 278, 680–686), for example Poly-Prep slides (Sigma Diagnostics), or aminosilanes, like Silane-Prep slides (Sigma), CMT GAPS slides (Corning), and Super Amine (Telechem), or membranes, like CAST slides or FAST slides (Schleicher & Schëll). For immobilization of amino-modified oligonucleotides, epoxy-modified surfaces, like ArrayLink Biochip (GeneScan Europe) or Epoxysilane slides (Quantifoil) are particularly preferred.

The nucleotide sequences can be bound and fixed on the carrier substrate via chemical or photochemical reactions or by electrostatic interactions. In a preferred form of embodiment of the invention, it is provided that the immobilization or fixing of the nucleic acid on the substrate surfaces used is accomplished via an electrostatic or a covalent binding. If the nucleic acids, for example, were produced synthetically and have a functional group, the nucleic acids can be bound covalently and fixed on the surface of the substrate material. (Lamture et al., 1994, *Nucl. Acids Res.*, 22, 2121–2125; Guo et al., 1994, *Nucl. Acids Res.*, 22, 5456–5465). According to the invention, the nucleic acids can also be covalently bound to the surface-activated substrate via a spacer or a cross-linking agent, for example, a bifunctional cross-linking agent. In a preferred form of embodiment of the invention it is provided that the binding of the nucleotide sequences on the substrate is done, in the case of polylysine-coated, aminosilane-coated, and membrane-coated nucleotide chips, by means of UV cross linking and, in case of epoxy modified chips, by means of a chemical reaction. The binding of the nucleic acids on the substrate can obviously also be done via photochemical reactions. In the case of such photolithographically produced nucleotide chips, a selective splitting off of the photosensitive protective group occurs by means of photolysis.

A further preferred form of execution of the present invention thus relates to processes for the production of the nucleotide chips, including the isolation and/or amplification of at least one nucleotide sequence, which codes a hyphen-specifically expressed protein of *Candida* and/or contains regulatory elements of this nucleotide sequence, or the chemical synthesis of this nucleotide sequence, the modification of the nucleotide sequence during or after the synthesis or amplification by the insertion of functional groups or spacer units, the application of an aqueous solution of the isolated or synthesized nucleotide sequence to a solid substrate material, and the immobilization of the nucleotide sequence on the substrate by means of chemical or photochemical reaction or electrostatic interaction.

A further particularly preferred form of execution of the invention, relates to protein chips containing a solid substrate and at least one hyphen-specific protein fixed on it, selected from the group consisting of:

(a) a protein with an amino acid sequence defined in SEQ ID No. 5, 6, 7, 8, 14, 16 or 18, or a fragment thereof, and (b) a protein with an amino acid sequence which has a sequence identity of at least 80% to one of the amino acid sequences defined in SEQ ID No. 5, 6, 7, 8, 14, 16 or 18, or to a fragment thereof.

In connection with the present invention, a protein chip is understood to mean a device which contains a plurality of different proteins or peptides in immobilized form and, with whose aid, a small amount of a ligand, e.g. of a protein or an antibody which can bind covalently or non-covalently to at least one protein or peptide fixed to the substrate, can be detected in a small sample liquid.

According to the invention, the protein chips contain proteins fixed on a solid substrate, said proteins being expressed only in the hyphally growing form of *Candida albicans*, or parts thereof. The protein chips according to the invention can thus, for example, be used for the detection of antibodies, which were formed in the body of an organism, in particular a mammal as a consequence of an immunization by antigen determinants of hyphally growing forms of *Candida*, in particular hyphen-specific *Candida* proteins. The binding of at least one antibody for blood, lymph, body secretions, or other body fluids of an organism to the protein chip according to the invention therefore makes possible the detection of a systemic *Candida* infection in this organism, said infection leading to the formation of the bound antibody. Moreover, the protein chips according to the invention can also be used in order, for example, to identify and isolate such proteins from *Candida*-infected materials as enter, in vivo, into interactions with the proteins contained on the protein chip. After identification and isolation of interacting proteins of this type, the protein chips, according to the invention, can also be used in order to identify substances of any type, which according to the invention, can inhibit or promote the interaction between the proteins and proteins interacting therewith. With the use of the protein chips according to the invention therefore, substances can be detected which are potentially suitable as medicaments for fighting *Candida* infections, in particular for the inhibition of the transition from yeast-like growth to hyphal growth of *Candida*.

In a particularly preferred form of embodiment of the invention, it is provided that the protein chip, according to the invention, can also include, along with the hyphen-specific proteins with the amino acid sequences represented in SEQ ID 5, 6, 7, 8, 14, 16, and 18, also derivatives, functional equivalents, or variants of these proteins. In connection with the present invention the phrase "derivatives, functional equivalents, or variants" is understood to mean, in particular, those derivatives of the proteins with the amino acid sequences specified in SEQ ID 5 to 8, 14, 16, and 18 which, while retaining the basic structure of these proteins, are obtained by substitution of atoms or molecule groups and their amino acid sequences are distinguished from the amino acid sequences specified in SEQ ID 5 to 8, 14, 16, and 18 at least one position and which essentially have a high degree of homology at the amino acid level. The term "homology" known to those skilled in the art denotes the degree of kinship between two polypeptides, said degree being determined by the extent of agreement between these polypeptides. Therein an agreement can mean an identical agreement, thus sequence identity, as well as a conservative amino acid exchange. Preferably derivatives, variants, or functional equivalents used according to the invention each have a sequence identity to one [of the] amino acid sequences specified in SEQ ID 5 to 8, 14, 16, and 18 of at least 80%, preferably 85%, and particularly preferably of over 90%, 95%, 97%, and 99% at the amino acid level. The deviations relative to the amino acid sequences represented in SEQ ID 5, 6, 7, 8, 14, 16 or 18 could have arisen, for example, by deletions, substitutions, insertions, additions, exchanges, or recombinations of the nucleotide sequences coding the amino acid sequences produced with technological means. However, they can be naturally occurring variations, for example, amino acid sequence changes arising in a natural manner. Derivatives or variants of the hyphen-specific proteins according to the invention can, for example, stem from clinical isolates of *Candida*.

Such derivatives, functional equivalents, or variants can be distinguished from the proteins with the amino acid sequences represented in SEQ ID 5, 6, 7, 8, 14, 16, and 18, for example, by an altered stability, specificity, a modified temperature, pH value, and/or concentration profile, an altered activity, and/or an altered effector pattern. Derivatives, functional equivalents, or variants can also occur in other conformations or have other subunits or pre-translational and/or post-translational modifications. Despite the differences which may be present, the hyphen-specific proteins with the amino acid sequences represented in SEQ ID 5, 6, 7, 8, 14, 16, and 18 and derivatives, variants, or functional equivalents thereof have nonetheless certain common characteristics such as activity, molecular weight, immunological reactivity, conformation, and/or physical properties such as running behavior in gel electrophoresis and their solubility and other things.

In an additional particularly preferred form of embodiment of the invention, it is provided that the protein chip according to the invention includes fragments of the proteins with the amino acid sequences specified in SEQ ID 5 to 8, 14, 16 or 18 or the proteins whose amino acid sequence has a sequence identity of at least 80% relative to one of the amino acid sequences defined in SEQ ID 5, 6, 7, 8, 14, 16, and 18. In connection with the present invention, "fragments" is understood to mean, in particular those isolated regions of a protein, which have fewer amino acids than the native protein but whose length is sufficient that the isolated fragment can exert one of the functions characteristic for the native protein such as binding capability to a second protein, a specific catalytic activity, and so on. In a particularly preferred form of embodiment of the invention, the fragment of a protein includes a protein region, which represents an antigen determinant or an epitope and thus is suitable to a particular degree for the binding of an antibody.

According to the invention, the hyphen-specific proteins, in particular the proteins with the amino acid sequences represented in SEQ ID 5, 6, 7, 8, 14, 16, and 18, which according to the invention, are immobilized on the protein chip, can have been isolated and purified from natural sources, for example, from *Candida*-infected tissues or specifically established *Candida* cultures with the use of customary processes known in the art. The proteins or fragments used can also be of synthetic origin. For example, peptides, that is fragments of the proteins according to the invention, can be produced with the aid of the process of Merrifield (1985, *Angew. Chem.* 97, 801). In a particularly preferred form of embodiment of the present invention the hyphen-specific proteins or peptides are produced by means of customary DNA recombination technologies. For example, the protein-coding nucleotide sequences according to the invention such as the sequences represented in SEQ ID 1, 2, 3, 4, 13, 15, and 17, or sequences hybridized therewith are inserted in suitable vectors with the use of customary processes of molecular biology and gene technology and cloned. Preferably, the insertion of the protein-coding nucleotide sequences, according to the invention, is done so that they are under the control of regulatory elements, i.e. are operationally connected with them. These regulatory elements assure the transcription and synthesis of translatable nucleic acid molecules in prokaryotic and eukaryotic cells. The regulatory elements can be promoters, enhancers, operators, silencers, and/or transcription termination signals. After transformation in suitable host cells, for example prokaryotic and eukaryotic cells such as bacteria, yeast, plant, insect, or mammal cells, these host cells can be cultivated in a suitable culture medium under such conditions as permit the formation of the hyphen-specific proteins coded by the protein-coding nucleotide sequence or a fragment thereof. Subsequently, the protein or fragment thereof can, with the use of a suitable process, be isolated from the host cell, or the medium in which the host cell was cultivated, and purified. However, for the production of the hyphen-specific proteins or fragments suitable in vitro transcription/translation systems can also be used. In a particularly preferred form of embodiment of the invention, the production of the hyphen-specific proteins or fragments thereof is done in bacterial expression systems wherein the protein preferably are obtained as GST fusion proteins, HIS-tag fusion proteins, pMAL fusion proteins, and so on.

As a solid substrate for the protein chips according to the invention, the same materials can be used as described above for the nucleotide chips according to the invention, for example glass, silicon dioxide, other silica materials, polymeric materials such as fluoropolymers, metal oxides, etc. can be used. These substrate materials are preferably pretreated before immobilization of the antibodies, for example, with silane coupling agents. In a preferred form of embodiment of the invention, the epoxy-modified substrate or membranes described by Joos et al, (Joos et al., 2000, *Electrophoresis*, 21, 2641–2650) are used.

According to the invention, it is provided that the binding and immobilization of the hyphen-specific proteins or fragments on the substrate material is done by means of chemical or photochemical reaction or electrostatic interaction. The hyphen-specific proteins, according to the invention and fragments thereof can, for example, be bound and immobilized on the substrate material by a plurality of customarily used functional groups and/or spacers or chemical cross-linking agents, such as bifunctional cross-linking agents. An overview of suitable functional groups which make possible a binding of proteins to silanized surfaces is found, for example, in Weetall, 1996, *Advances in Molecular and Cell Biology*, Vol. 15A, 161–192, JAI Press Inc. In case the protein to be immobilized is present as GST fusion protein, the binding of the protein to the substrate is done via GSH units present on the surface of the substrate. The immobilization of a pMAL fusion protein can be done via MBP units on the surface of the substrate. If the protein to be immobilized is HIS-tag fusion protein, the immobilization can be done via $Ni^{2+}$-nitrilotriacetic acid surfaces (Ni-NTA) (Adachi, et al., *Proc. Nat. Acad. Sci.* USA, 97, 7243–7247).

An additional preferred form of embodiment of the present invention thus relates to processes for the production of protein chips including the isolation of at least one hyphen-specifically expressed *Candida* protein from a suitable source or the chemical synthesis or recombinant production of this protein or a fragment thereof, the modification of the protein or fragment during or after the isolation, synthesis or production by the insertion of functional groups or spacer units, the application of an aqueous solution of the isolated or synthesized protein on a solid substrate material by means of chemical or photochemical reaction or electrostatic interaction.

A particularly preferred form of embodiment of the present invention, relates to an antibody chip including a solid substrate and at least one antibody fixed thereon which is directed specifically against a protein with the amino acid sequence represented in SEQ ID 5, 6, 7, 8, 14, 16 or 18, or a fragment thereof or a derivative thereof.

Since the antibodies fixed on the antibody chip, according to the invention, are directed specifically against hyphen-specific *Candida* proteins, the presence of hyphally growing *Candida* cells in sections of skin or mucus membrane infected by fungus, organ biopsies, or body fluids can be detected with the use of a chip of this type. For example, proteins can be extracted from the aforementioned samples and, after marking with the antibody chip, according to the invention, incubated. The binding of at least one marked protein on the antibody chip, according to the invention, thus shows that hyphally growing *Candida* is present in the sample examined.

In connection with the present invention, the term "antibody" is understood to mean a polypeptide, which is coded by one or more immunoglobin genes and recognizes specific structures on an antigen, in particular an antigen determinant or an epitope, and can bind specifically thereto. The term "antibody" does not include only a complete immunoglobin but rather also a series of fragments, which are available by means of splitting with various peptidases. The term "antibody" also includes modified antibodies such as oligomers, reduced, oxidized, and marked antibodies. "Antibody" also includes antibody fragments, which were produced by modification of intact antibodies as well as with the use of DNA recombination technologies. In connection with the present invention "antibody" also includes, in particular, fragments such as Fab, F(ab')$_2$, or Fvm, which can bind to an antigen determinant. The Fab fragment can be produced by splitting of the intact antibody with the enzyme papain whereby an intact light chain with a part of a heavy chain is obtained. F(ab')$_2$ can be produced by treatment of the intact antibody with pepsin without subsequent reduction. F(ab')$_2$ is a dimer consisting of two Fab' fragments. Fv is an antibody fragment produced by gene technology, said antibody fragment including the variable region of the light chain and the variable region of the heavy chain. Processes for the production of such fragments have been described, for example, by Harlow and Lane in "Antibodies: A Laboratory Manual", 1988, Cold Spring Harbor Laboratory, New York.

The phrase "antibody which is directed against a protein" or "antibody, which binds specifically to a protein" means that an antibody can recognize, under defined immune test conditions, an antigen determinant or an epitope of a protein and can bind thereto by means of its paratope. Antigen determinants usually consist of chemically active molecule groups such as amino acids or sugar side chains on the surface of an antigen, e.g. a protein, and have a characteristic three-dimensional structure. Under defined conditions an antibody thus preferably binds only to a certain protein while no noteworthy binding to other proteins in the same sample occurs.

An antibody immobilized according to the invention on an antibody chip can thus bind to a protein, peptide, carbohydrate, proteoglycan, and/or a lipid complex, which is in specific relation with the hyphen-specific protein used according to the invention. According to the invention, an antibody used can be directed against structures, which are to be considered as post-translational modifications of the hyphen-specific proteins.

According to the invention, it is provided that the antibody chip contains monoclonal as well as polyclonal antibodies, which are able to specifically identify, and in given cases bind to, a structure of a hyphen-specific protein, according to the invention.

According to the invention, the monoclonal and polyclonal antibodies contained on the antibody chip can be produced and isolated with the use of processes well-known in the art. The processes for the production of monoclonal antibodies with the use of hybridoma technology are described, for example, in "Hybridoma Techniques" (1980) or in the U.S. Pat. No. 4,341,761, No. 4,399,121, or No. 4,472,500.

As substrate material for the immobilization of the antibodies, the materials named above for protein chips such as glass, silicon dioxide, nylon, acryl amide derivatives, silica materials, polymeric materials, such as fluoropolymers, metal oxides, etc. can be used. These substrate materials are preferably pretreated before immobilization of the antibodies, for example, with silane coupling agents. In a preferred form of embodiment of the invention, the epoxy-modified substrate or membranes described by Joos et al. (Joos et al., 2000, Electrophoresis, 21, 2641–2650) are used.

According to the invention, it is provided that the binding of the antibodies, directed against specific hyphen-specific proteins, on the substrate is done via a chemical or photochemical reaction or via electrostatic interactions. As described above for protein chips, the antibodies used, according to the invention, e.g. with the aid of a plurality of customarily used functional groups and/or spacers or chemical cross-linking agents such as such as bifunctional cross-linking agents, are bound and immobilized on the substrate material.

An additional preferred form of embodiment of the present invention, thus relates to processes for the production of antibody hips including the gene-technological production, isolation, or synthesis of at least one antibody directed against a hyphen-specific Candida protein or fragments thereof, the modification of the antibody or fragment thereof during or after the isolation, synthesis, or production by the insertion of functional groups or spacer units, the application of an aqueous solution of the isolated or synthesized protein to a solid substrate material by means of chemical or photochemical reaction or electrostatic interaction.

An additional particularly preferred form of embodiment of the present invention, relates to an antibody chip including a solid substrate and at least one antibody fixed thereon which is directed specifically against a protein with the amino acid sequence represented in SEQ ID 5, 6, 7, 8, 14, 16 or 18. An antibody chip of this type therefore includes antibodies, which are directed against the aforementioned antibody and can recognize and bind to it specifically. The use of an antibody makes possible the detection of antibodies against hyphen-specific proteins of Candida in the blood, the lymph, in body secretions, or other body fluids of an organism and thus the detection of a systemic Candida infection in this organism, which has lead to the formation of the antibody contained in the sample.

The present invention also relates to a diagnostic composition including at least one nucleotide chip, according to the invention, a protein chip, according to the invention and/or an antibody chip, according to the invention. The invention, thus, also includes diagnostic kits which, according to the invention, contain the biochips i.e. nucleotide chips, protein chips, and antibody chips, suitable buffer systems, and suitable marking systems.

The invention relates in a particularly preferred form of embodiment to processes for the diagnosis of diseases caused by types of Candida, in particular diseases caused by Candida albicans wherein a sample to be tested is brought, in a suitable medium, into contact with a nucleotide chip according to the invention, a protein chip according to the invention, and/or an antibody chip, according to the invention and an interaction between the sample to be tested and at least one of said biochips is detected. The process, according to the invention, for the diagnosis of Candida diseases is based on the detection of the presence of nucleotide sequences, proteins, antibodies, or fragments thereof which, according to the invention, are in association with the hyphen-specific proteins in samples such as skin or mucus membrane swabs, organ biopsies, body secretions, blood, lymph, or other body fluids etc. which show fungal infection or are suspected of being infected.

In connection with the present invention, the phrase "diseases, disease states, or infections caused by types of Candida" is understood to mean those diseases, which are causes exclusively by types of Candida, in particular, however, by Candida albicans. The term thus also includes all the diseases, which are caused by types of Candida such as C. tropicalis, C. krusei, C. parapsilosis, and C. guilliermondii, or Torulopsis (Candida) galabrata. According to the invention, this term is also understood to include diseases or disease states which primarily have other causes and in which the types of *Candida* are only a part of the disease profile or additional symptoms are added, for example, opportunistic infections. The phrase "diseases, disease states, or infections caused by types of *Candida*" includes, in particular, those diseases such as *Candida* mycoses or candidoses, which can be subdivided essentially into three principal forms. The first principal form of candidosis is characterized by a saprophytic infestation of the skin and mucus membranes, in particular in the external genitalia, in the mouth, region of the nasal cavity, and in the digestive tract. The second principal form of candidosis includes infections of the skin and mucus membranes and is to a significant extent promoted by factors such as pregnancy, diabetes mellitus, serious diseases or traumas, cytostatics and antibiotic therapy as well as alcoholism. The third principal form of candidosis includes deep organ mycoses in immune-suppressed patients with cellular immune deficiency, in particular in the region of the respiratory tract, more rarely as *Candida endocarditis, Candida meningitis, Candida nephritis, Candida endophthalmitis.*

Based on the hyphen specificity and, associated therewith, the correlation to a *Candida*-caused disease profile, the presence of nucleotide sequences, proteins, antibodies, or fragments thereof which are in association with the hyphen-specific proteins according to the invention points toward a *Candida*-caused disease. The detection of the aforementioned substances is done by binding and/or hybridization of at least one of the biochips, according to the invention, which specifically recognize the substances to the detected.

If nucleotide sequences in association with the hyphen-specific proteins are detected in a sample, their detection, according to the invention, is done by hybridization with the nucleotide chip. For this, nucleic acids, by way of example DNA or mRNA, are isolated from a sample or from a specifically established culture and/or and amplified, for example, by means of PCR processes. The nucleic acids extracted are subsequently marked, for example, with fluorescent dyes, enzymes, or radioactive groups. If the extracted or marked DNA hybridizes with the nucleotide chip, then this shows the presence of *Candida* in the sample examined. If the extracted mRNA hybridizes with the nucleotide chip according to the invention, then this points to the fact that the sample contains hyphally growing forms of *Candida*.

If hyphen-specific *Candida* proteins are to be detected in an examined sample, proteins from the sample are extracted and marked and subsequently incubated with the antibody chip according to the invention, said antibody chip containing antibodies against hyphen-specific proteins. According to the invention, the binding of at least one marked protein on the antibody chip points to the presence of hyphally growing *Candida* cells. According to the invention, the detection of antibodies against *Candida* proteins in body fluids can be done with the use of the protein chip as well as the antibody chip, which, according to the invention, contains the antibodies, which are directed against the antibodies against hyphen-specific proteins.

The present invention also relates to processes for finding and identifying substances, which are therapeutically effective against *Candida*-caused diseases wherein a substance to be tested is brought, in a suitable medium, into contact with a nucleotide chip according to the invention, a protein chip according to the invention, or an antibody chip according to the invention and an interaction between the sample to be tested and at least one of said biochips is detected. Thus, according to the invention, the nucleotide chips and protein chips as described above, are used in order to identify substances, e.g. proteins, which in vivo bind to nucleotide sequences, which code the hyphen-specifically expressed proteins or regulate the expression of these proteins or bind to the hyphen-specific proteins themselves. Such binding substances, in particular proteins, can potentially be suitable as medicaments against *Candida*-caused diseases if they, for example, are able, by binding to regulatory nucleotide sequences, to inhibit or restrict the transcription of hyphen-specific proteins or if they are able, by binding the hyphen-specific proteins, to inhibit or restrict their activity. If such substances, which, according to the invention, bind to the nucleotide chips and protein chips induce or promote transcription of the hyphen-specific proteins or favor the activity of hyphen-specific proteins of this type of protein, the biochips, according to the invention, can be used in order to identify additional substances which are able to influence or inhibit the interaction between a hyphen-specific protein or the nucleotide sequence coding it and the substance binding thereto, in particular a binding protein. Such substances are also potentially suitable as medicaments for the treatment of *Candida*-caused diseases.

The present invention will be explained by the following sequence protocol and the following figures and examples.

The sequence protocol is part of this description and contains the sequence protocols SEQ ID No. 1 to 18. Each of the amino acid sequences cited below was derived from the corresponding DNA sequence and then partially verified by sequencing of the isolated proteins.

SEQ ID No. 1 represents the DNA sequence from Contig4-2149 coding Cap33a.

SEQ ID No. 2 represents the DNA sequence from Contig4-2501 coding Cap33b.

SEQ ID No. 3 represents the DNA sequence from Contig4-2069 coding Cap18p.

SEQ ID No. 4 represents the DNA sequence from Contig4-2069 coding Cap19p.

SEQ ID No. 5 represents the amino acid sequence of Cap33a.

SEQ ID No. 6 represents the amino acid sequence of Cap33b.

SEQ ID No. 7 represents the amino acid sequence of Cap18p.

SEQ ID No. 8 represents the amino acid sequence of Cap19p.

SEQ ID No. 9 represents the entire DNA sequence of Contig4-2149.

SEQ ID No. 10 represents the entire DNA sequence of Contig4-2501.

SEQ ID No. 11 represents the entire DNA sequence of Contig4-2069.

SEQ ID No. 12 represents the promoter region of Cap18p and Cap19p.

SEQ ID No. 13 represents the DNA sequence from Contig5-3226 coding Cap 15p.

SEQ ID No. 14 represents the amino acid sequence of Cap15p. Cap 15p is probably a nucleoside diphosphate kinase.

SEQ ID No. 15 represents the DNA sequence from Contig4-2178 coding Cap20p.

SEQ ID No. 16 represents the amino acid sequence of Cap20p. Cap20p is probably a glutathione peroxidase.

SEQ ID No. 17 represents the DNA sequence from Contig5-2806 coding Cap40p.

SEQ ID No. 18 represents the amino acid sequence of Cap40p, Cap40p is probably a fructose biphosphate aldolase.

FIG. 1 shows, in its left part, microscopic pictures of the virulent, hyphally growing *Candida albicans* strain Sc5315 and the non-virulent *Candida* strain Can34 (Δcph1Δefg1) growing in the manner of a yeast. From both strains RNA was isolated and rewritten into cDNA. The marked cDNA was hybridized with a nucleotide chip according to the invention, on which nucleotide sequences coding CAP33, CAP19, and CAP18 were fixed. The results of this hybridization are to be seen in the right part of FIG. 1. While the cDNA from the non-virulent strain hybridized with none of the nucleotide sequences contained on the nucleotide chip, the cDNA of the virulent strain showed strong hybridization signals with all three immobilized nucleotide sequences. If, however, the *C. albicans* strain Sc5315 is cultivated under conditions under which no hyphae arise, the same result is obtained as for the non-virulent strain Can34 (Δcph1Δefg1).

Figure 2:
FIG. 2a shows microscopic pictures of the virulent, hyphally growing *Candida albicans* strain Sc5315 and the non-virulent *Candida* strain Can34 (Δcph1Δefg1) growing in the manner of a yeast.
FIG. 2b show the results of a Northern blot analysis with the use of RNAs from these two strains which previously were cultivated either YPD medium or in α-MEM medium.
Figure 2:
Figure 2:
Figure 2:
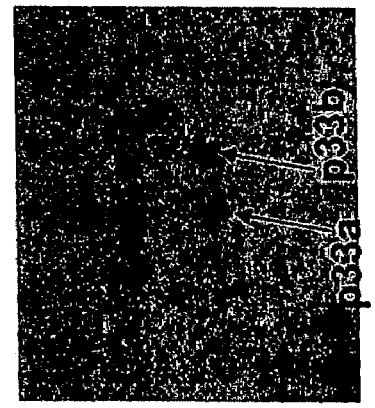
Figure 2:
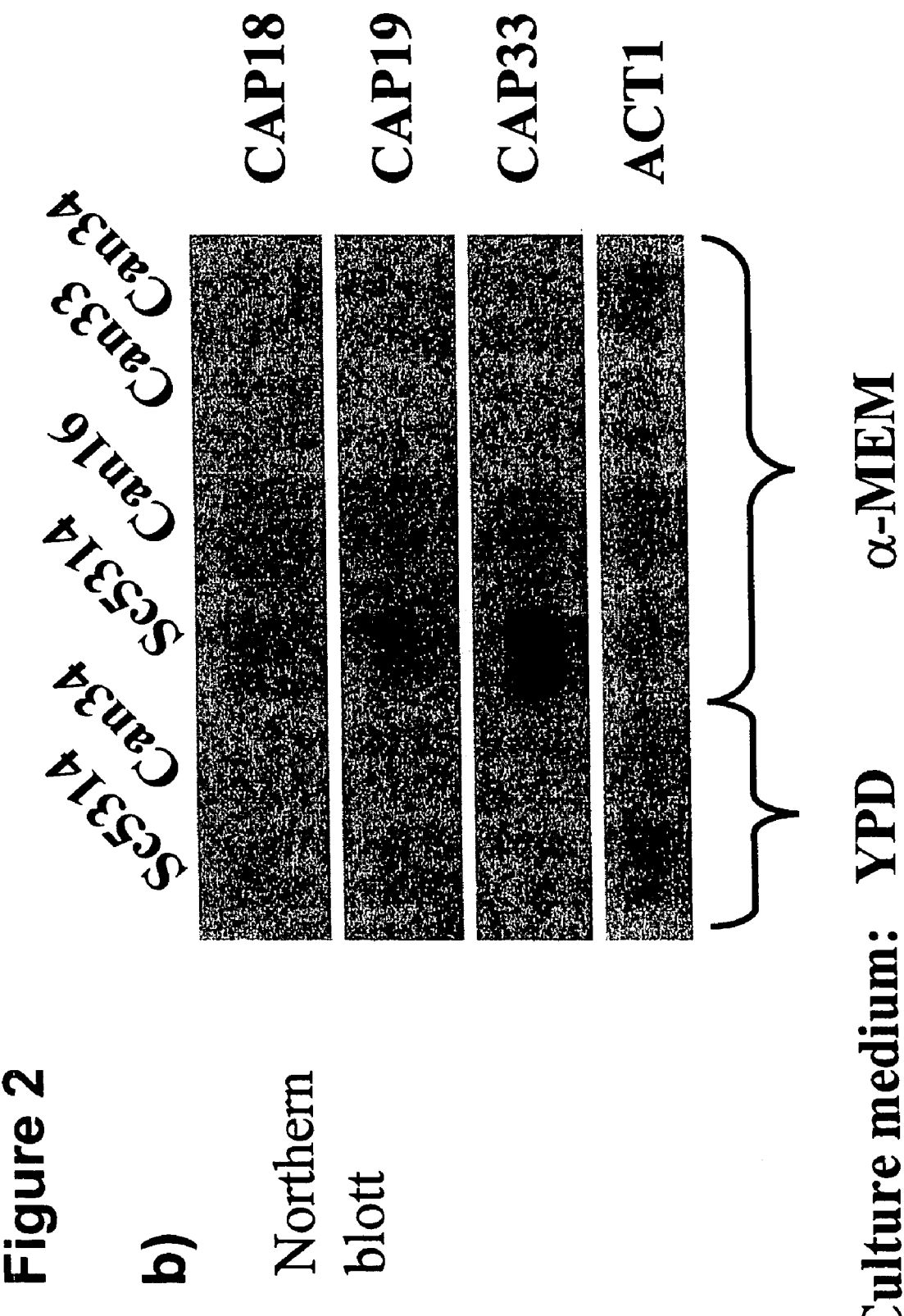

FIG. 2a shows microscopic pictures of the virulent, hyphally growing *Candida albicans* strain Sc5315 and the non-virulent *Candida* strain Can34 (Δcph1Δefg1) growing in the manner of a yeast. Under this, presentations of differential proteome analyses of the two strains after cultivation in α-MEM medium are shown. From these presentations it follows that Sc5314 on cultivation in α-MEM medium expresses the proteins p33a and p33b, but Can34 (Δcph1Δefg1) does not.

FIG. 2b show the results of a Northern blot analysis with the use of RNAs from these two strains which previously were cultivated either YPD medium or in α-MEM medium. Also included were RNAs from the virulent strain Can16 (Δcph1) and the strain Can33 (Δefg1), which shows no formation of hyphae and has a sharply reduced virulence, where both strains were cultivated before RNA extraction in α-MEM medium. On hybridization with cap18-specific, cap-19-specific [sic], and cap33-specific probes, hybridization signals were found with the RNAs isolated from the strains Sc5314 and Can16 cultivated in α-MEM medium. The RNA isolated from the strain Sc5314 cultivated in YPD medium showed on the contrary no hybridization signals. The RNA from the non-virulent strain Can34 (cultivated either in YPD or in α-MEM medium) also showed no hybridization signals. The same result was also obtained in the RNA, which was isolated from the strain Can33 cultivated in α-MEM medium. As a control an actin-specific probe (ACT1) was used.

Figure 3:
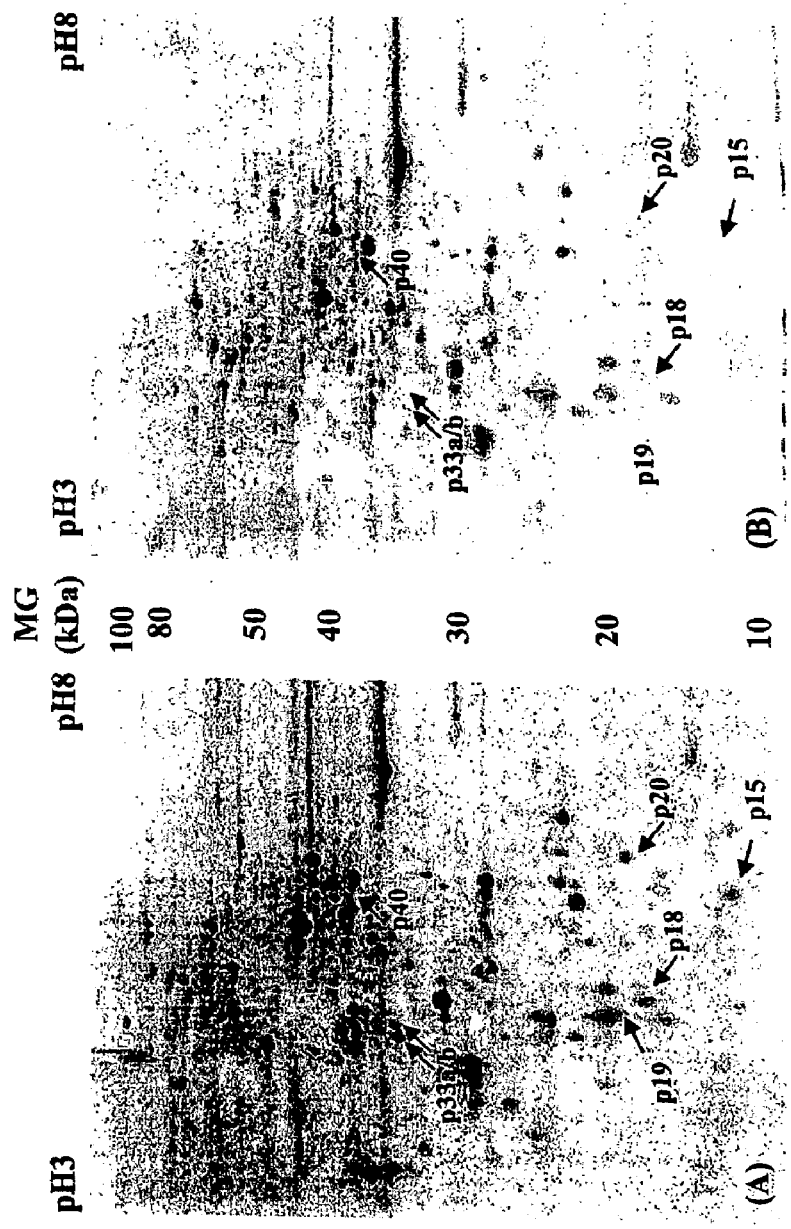
FIG. 3 shows the results of 2D gel electrophoreses of protein extract from the strains Sc5315 and Can34 (Δcph1Δefg1) cultivated in α-MEM medium.

FIG. 3 shows the results of 2D gel electrophoreses of protein extract from the strains Sc5315 and Can34 (Δcph1Δefg1) cultivated in e-MEM medium. While Sc5315 expresses the hyphen-specific proteins p33a, p33b, p40, p15, p18, p19, and p20, these proteins are not expressed in Can34 (Δcph1Δefg1).

Additional advantageous developments of the invention are described in the subordinate claims.

The invention will be described in more detail with the aid of the following examples.

EXAMPLE 1

The Isolation of the Proteins

The proteins were isolated from the clinical isolate Sc5314 by differential 2D gel electrophoresis as follows:

For the isolation of the proteins the virulent *Candida albicans* strain Sc 5314 and the non-virulent *Candida albicans* strain Can34 (HLC69) (Lo et al., 1997, *Cell*, 90, 939–949) were covered simultaneously in complete medium (YPD: 20 g/l bactopeptone, 10 g/l yeast extract, 0.15 g/l L-tryptophan) over night, inoculated, in α-MEM medium (#22571 Life technologies/Gibco), with 2% glucose extract (1:100), and incubated for 24 hours at 37° C. on a rotary agitator. The cells thus obtained were pelletized and closed up in a saline buffer not containing detergent (PGSK buffer: 0.52 g/l Na$_2$HPO$_4$.H$_2$O, 8.8 g/l NaH$_2$PO$_4$.2H$_2$O, 2.8 g/l NaCl, 0.372 g/l KCI, 11 g/l glucose) with glass beads. The protein extract isolated from this was separated by means of isoelectric focusing and thereafter by means of SDS PAGE. The gels were dyed with silver (cf. FIG. 2a) or Coomassie (cf. FIG. 2b). The protein spots, which were visible only in one of the two gels were cut out of the Coomassie-dyed gels and their sequence determined. It could be shown that the identified proteins were formed only in Sc5314 in α-MEM medium (FIGS. 2a and 3).

Based on the amino sequence, which was unambiguously determined by Edmann decomposition of tryptic fragments of the protein, the corresponding DNA sequence could be identified via data base comparisons. The DNA sequences as well as the flanking regions were amplified and cloned by PCR from genomic DNA of Sc5314. Furthermore, the corresponding DNA sequence from genomic libraries (Liu et al., 1995, *Science*, 266, 1723–1726) was isolated by means of hybridization of the radioactively marked fragments obtained by PCR.

The coding sequences for each of the seven identified proteins were removed from the cloned PCR fragments, by means of PCR, and replaced by selection markers (URA3) (Fonzi and Irwin, 1993, *Genetics*, 134, 717–728). These constructs are used for the deletion of the coding sequence in *C. albicans*. Furthermore, the open reading frame for all seven proteins as well as the termination sequences were isolated by means of PCR and cloned in vectors with regulable PCK1 and MET3 promoters (Leuker et al., *Gene*, 1997, 19, 192(2), 235–40; Care et al., *Mol. Microbiol.*, 1999, 34(4), 792–8.) for the expression in *C. albicans* or with regulable GAL1-10 and MET25 promoters (Mumberg et al., *Nucleic Acids Res.* 1994, 25, 22 (25), 5767–8.) for the expression in *S. cerevisiae* and in suitable vectors (PMAL, PGEx, etc.) for expression of the proteins in bacteria.

EXAMPLE 2

Detection of the Hyphen-Specific Expression of the Proteins According to the Invention The regulation of the hyphen-specifically expressed proteins takes place at the transcription level since the mRNA for all seven proteins can be detected only in 5c5314 cultures washed in α-MEM, not in Sc5314, which was cultivated in complete medium or in the non-virulent strain Can34 (Δcph1Δefg1) that was cultivated in complete medium or α-MEM medium.

FIG. 2b shows as an example a Northern analysis of RNA from the strains Sc5314 and Can34 (Δcph1Δefg1) cultivated in complete medium. In this Northern analysis moreover RNA of the strains Can16 (Δcph1) cultivated in α-MEM medium and Can33 (Δefg1) (Lo et al., 1997, *Cell*, 90, 939–949) were plotted. Can16 (Δcph1) was described as a strain, which has a virulence comparable to Sc5314 and shows the formation of hyphae. Can33 (Δefg1) shows on the contrary no formation of hyphae and its virulence is sharply reduced (Lo et al., 1997, *Cell*, 90, 939–949).

In the cultivated strain Sc5314, which was cultivated in α-MEM medium, the corresponding mRNAs can be detected with Cap33-specific, Cap18-specific, and Cap19-specific probes. On the contrary, no corresponding mRNAs can be detected with the above-mentioned probes in Sc5314 that was cultivated in YPD medium. In the virulent strain Can16 cultivated in α-MEM medium the corresponding mRNAs can also be detected with the use of the probes. The non-virulent strain Can34 (Δcph1Δefg1) cultivated either in YPD medium or α-MEM medium contains no corresponding mRNAs. The strain Can33 cultivated in α-MEM medium also contains no corresponding mRNAs.

The results of these Northern blot analyses show on the one hand the hyphen-specific expression of the proteins with SEQ D No. 5, 5 [sic], 7, 8, 14, 16, and 18 in the virulent strains Sc5314 and Can16. On the other hand these results show that the hyphen-specific expression of these proteins is regulated principally at the transcription level. This is significant for use as diagnostic means since the presence, in a sample to be tested, of mRNA, which is associated with one of the aforementioned hyphen-specific proteins points toward the occurrence of hyphally growing virulent forms of *Candida* in this sample.

Protein extracts from the strains Sc5314 and Can34 (Δcph1Δefg1), which were cultivated in α-MEM medium, were accordingly subjected to a 2D gel electrophoresis according to customary processes. As is to be seen in FIG. 3 the hyphen-specifically expressed proteins p15, p18, p19, p20, p33a, p33b, and p40 can only be detected in the hyphally growing strain Sc5314 but not in the non-virulent strain Can34 (Δcph1Δefg1). In FIG. 2*a*, moreover it is shown that the strain Sc5314 cultivated in α-MEM medium produces the proteins Cap33a and Cap33b, the strain Can34 does not.

EXAMPLE 3

Detection of the Hyphen-Specific Expression of the Proteins Coding Nucleotide Sequences by Means of Nucleotide Chips On a substrate surface coated with poly-L-lysine, nucleotide sequences are fixed, which code the hyphen-specific proteins CAP33, CAP19, and CAP18. The nucleotide chip thus obtained was hybridized under customary hybridization conditions with cDNAs which were produced from mRNA of the hyphally growing strain Sc5315 and the non-virulent strain Can34 (Δcph1Δefg1) growing in a yeast-like manner. The results of this hybridization are presented in FIG. 1. While the cDNA from the non-virulent strain hybridized with none of the nucleotide sequences contained on the nucleotide chip, the cDNA of the virulent strain showed strong hybridization signals with all three immobilized nucleotide sequences. This experiment shows that with the use of a nucleotide chip according to the invention specific nucleic acids can be detected and that thereby hyphally growing virulent *C. albicans* strains can be distinguished from non-hyphally growing non-virulent *C. albicans* strains.

The invention claimed is:

1. A nucleotide chip including a solid substrate and at least one polynucleotide fixed thereon, wherein the polynucleotide is suitable for the identification of a gene encoding a hyphen-specific protein and wherein the polynucleotide comprises the nucleotide sequence of SEQ ID No. 1.

2. A diagnostic composition containing at least one nucleotide chip according to claim 1.

3. A nucleotide chip according to claim 1, wherein the polynucleotide comprises an, RNA, or PNA sequence.

4. A diagnostic composition containing at least one nucleotide chip according to claim 3.

* * * * *

SEQUENCE LISTING

<160> NUMBER OF SEQ ID NOS: 18

<210> SEQ ID NO 1
<211> LENGTH: 900
<212> TYPE: DNA
<213> ORGANISM: Candida albicans

<400> SEQUENCE: 1

```
atgtctaaag tctcaattac tatcatcggt ttgaatggtt tcttaggtaa accagttctt      60
gaagctatca attctggtat ttttgatgat aagatcaact tcccaatcaa ggcaattacc     120
agaaaggaac cagaaactaa gaatgacaaa attgaatatg ttgtttctga aatcaatgaa     180
gaatcaatta aatcaacttt gagccaaaaa ttatctggta ctgatgttat tattgaatta     240
attggtccaa atccagaggc tttcgccaat atcgaaaatt tagttgatgc aattaaacca     300
aaattattta tcccatcaca atttggtact gatattccta aagttgatga atatgctcca     360
gggtttttag gaattaaaac tcaacattca gaaaatgtca gaaaatcagg agttaaagtt     420
gttgatatta taacttcgtt atttgctgtt ccaggagctt ttctttatga atgggttggt     480
tcaactggta ttaatgctga agacagaact gttaaactca ttggtgacat taatcaacaa     540
tttgatattt ctaaattaga agatgttggt aaagctgtac tttctattgc tactaatcct     600
aatccaagag aattaccaga taccattaga attggttctg atagaattac tgttaaagat     660
gtaattgata gatactctaa agatcataat gttgaattga aaattgtttc agaacaatct     720
gcagaagacg ccaagaaaga gtttactgaa tctttgaaag ttggttttga tggtgataaa     780
ttcttatggt atttacaagt tattgctgct caaggtttag ataaaggttt actctccagt     840
aaattggata atgaattggt taatccaggt gaatctttat ggaaatgggg caagtactaa     900
```

<210> SEQ ID NO 2
<211> LENGTH: 900

<212> TYPE: DNA
<213> ORGANISM: Candida albicans

<400> SEQUENCE: 2

```
atgtctaaag tctcaattac tatcatcggt ttgaatggtt tcttaggtaa accagttctt      60
gaagctatca attctggtat ttttgacgat aaaatcaatt tcccaattaa agctattaca    120
agaaaagaac cggaaactaa aaatgacaaa attgaatacg ttgtttctga atcaatgaa     180
gaatcaatta aatcaacctt gagccaaaaa ttatccggta ctgatgttat tattgaatta    240
attggtccaa atccagaggc tttcgctaat atcgaaaaat taattgatgc aattaaacca    300
aaattattca ttccatcaca atttggtact gatattccta agttgatga atatgctcca     360
gggttttttag gaatcaaaac tcaacattca gaaaatgtca gaaaattagg agttaaagtt    420
gttgatatta aacttcgtt atttgctgtt ccaggagctt ttctttatga atgggttggt     480
tcaactggta tcaatgctga tgacaaaact gttaaactta ttggtgacat taatcaacaa   540
tttgatattt ctaaattaga agatgttggt aaagctgtac tttctattgc tactaatcct    600
aatccaagag aattaccaga taccattaga attggttctg atagaattac tgtcaaagat    660
gtcattgata gatattctaa agatcataat gttgaattga agttgtttc tgaacaatct     720
gcagaagatg ccaagaaaga gtttactgaa tcttgaaag ctggttttga tggtgagaaa     780
ttcttatggt atttacaagt tattgctgct caaggtttag ataaaggttt actctccagt    840
aaattggaca cgaattggt caacccaggt gagtctttat ggaaatgggg caagtactaa    900
```

<210> SEQ ID NO 3
<211> LENGTH: 501
<212> TYPE: DNA
<213> ORGANISM: Candida albicans

<400> SEQUENCE: 3

```
atggcctcct cagtaaagtt ggctacggca cttaaacaac gtgctatatt gacaaaagaa      60
ttgtctgaat tagatgataa aatacaatct tcattgattc tgcaagttgg tatgaaaaaa    120
atcaatgatc cagataaatt gtatttagat tatgttgcta atctcaaga attggctaaa     180
ttggtatcat caataaatta tactaataat ataactccaa ttgaacttga tttgacaatg    240
ggaaagtatg ataatactat aaaaacaatt aatgatgcat taatttgtcg agaccgaata    300
tttaaaaaat tacaatttgt gaaaaaaata tcaacagcag gtaaagaaca accattagat    360
tccaaagatc aaattaaatt tgtatcattt attgatgttg ataaatatga tacttttggcc   420
caagaattaa atactcaatt tgagaatttg aatttgaaat tacaagaaat aaattggcaa    480
gttgatcttg ttgagatata a                                              501
```

<210> SEQ ID NO 4
<211> LENGTH: 486
<212> TYPE: DNA
<213> ORGANISM: Candida albicans

<400> SEQUENCE: 4

```
atgaaattag ctgaagcatt aaatttaaaa aagaacttgg aaagagatgc tggtgaactt      60
aaatcattaa ttcttaaatg ttgtcaagct caaactggcg aaaacccttcc atttgatcct   120
aatgaattat ttgaacaata tgaagaaatt gataaattaa ttactgatat aactattaaa    180
atacaacgaa ccaataatga aataagtttt gcctatgata tgataataa gtctaatgaa     240
gaaccacttc gatcaatgac acaagctatt gctgatattg atgatttaga aagacaaatc    300
```

```
aatgtgacag atgatataat tcataatggt attattacaa aactgtattc gaccaagaag    360
attgctgatg tgtcacatgt tgacgtggtt gcatatgaca agacaagaaa gaaaatgaat    420
gagagattag ataaattaaa acttcgtata cagtcggcaa attgggaatt tgatctaatt    480
gattaa                                                               486
```

<210> SEQ ID NO 5
<211> LENGTH: 299
<212> TYPE: PRT
<213> ORGANISM: Candida albicans

<400> SEQUENCE: 5

```
Met Ser Lys Val Ser Ile Thr Ile Ile Gly Leu Asn Gly Phe Leu Gly
  1               5                  10                  15

Lys Pro Val Leu Glu Ala Ile Asn Ser Gly Ile Phe Asp Asp Lys Ile
             20                  25                  30

Asn Phe Pro Ile Lys Ala Ile Thr Arg Lys Glu Pro Glu Thr Lys Asn
         35                  40                  45

Asp Lys Ile Glu Tyr Val Val Ser Glu Ile Asn Glu Glu Ser Ile Lys
     50                  55                  60

Ser Thr Leu Ser Gln Lys Leu Ser Gly Thr Asp Val Ile Ile Glu Leu
 65                  70                  75                  80

Ile Gly Pro Asn Pro Glu Ala Phe Ala Asn Ile Glu Asn Leu Val Asp
                 85                  90                  95

Ala Ile Lys Pro Lys Leu Phe Ile Pro Ser Gln Phe Gly Thr Asp Ile
            100                 105                 110

Pro Lys Val Asp Glu Tyr Ala Pro Gly Phe Leu Gly Ile Lys Thr Gln
        115                 120                 125

His Ser Glu Asn Val Arg Lys Ser Gly Val Lys Val Val Asp Ile Ile
    130                 135                 140

Thr Ser Leu Phe Ala Val Pro Gly Ala Phe Leu Tyr Glu Trp Val Gly
145                 150                 155                 160

Ser Thr Gly Ile Asn Ala Glu Asp Arg Thr Val Lys Leu Ile Gly Asp
                165                 170                 175

Ile Asn Gln Gln Phe Asp Ile Ser Lys Leu Glu Asp Val Gly Lys Ala
            180                 185                 190

Val Leu Ser Ile Ala Thr Asn Pro Asn Pro Arg Glu Leu Pro Asp Thr
        195                 200                 205

Ile Arg Ile Gly Ser Asp Arg Ile Thr Val Lys Asp Val Ile Asp Arg
    210                 215                 220

Tyr Ser Lys Asp His Asn Val Glu Leu Lys Ile Val Ser Glu Gln Ser
225                 230                 235                 240

Ala Glu Asp Ala Lys Lys Glu Phe Thr Glu Ser Leu Lys Val Gly Phe
                245                 250                 255

Asp Gly Asp Lys Phe Leu Trp Tyr Leu Gln Val Ile Ala Ala Gln Gly
            260                 265                 270

Leu Asp Lys Gly Leu Leu Ser Ser Lys Leu Asp Asn Glu Leu Val Asn
        275                 280                 285

Pro Gly Glu Ser Leu Trp Lys Trp Gly Lys Tyr
    290                 295
```

<210> SEQ ID NO 6
<211> LENGTH: 299
<212> TYPE: PRT
<213> ORGANISM: Candida albicans

<400> SEQUENCE: 6

```
Met Ser Lys Val Ser Ile Thr Ile Ile Gly Leu Asn Gly Phe Leu Gly
 1               5                  10                  15

Lys Pro Val Leu Glu Ala Ile Asn Ser Gly Ile Phe Asp Asp Lys Ile
                20                  25                  30

Asn Phe Pro Ile Lys Ala Ile Thr Arg Lys Glu Pro Glu Thr Lys Asn
            35                  40                  45

Asp Lys Ile Glu Tyr Val Val Ser Glu Ile Asn Glu Glu Ser Ile Lys
        50                  55                  60

Ser Thr Leu Ser Gln Lys Leu Ser Gly Thr Asp Val Ile Ile Glu Leu
65                  70                  75                  80

Ile Gly Pro Asn Pro Glu Ala Phe Ala Asn Ile Glu Lys Leu Ile Asp
                85                  90                  95

Ala Ile Lys Pro Lys Leu Phe Ile Pro Ser Gln Phe Gly Thr Asp Ile
            100                 105                 110

Pro Lys Val Asp Glu Tyr Ala Pro Gly Phe Leu Gly Ile Lys Thr Gln
        115                 120                 125

His Ser Glu Asn Val Arg Lys Leu Gly Val Lys Val Asp Ile Ile
    130                 135                 140

Thr Ser Leu Phe Ala Val Pro Gly Ala Phe Leu Tyr Glu Trp Val Gly
145                 150                 155                 160

Ser Thr Gly Ile Asn Ala Asp Asp Lys Thr Val Lys Leu Ile Gly Asp
                165                 170                 175

Ile Asn Gln Gln Phe Asp Ile Ser Lys Leu Glu Asp Val Gly Lys Ala
            180                 185                 190

Val Leu Ser Ile Ala Thr Asn Pro Asn Pro Arg Glu Leu Pro Asp Thr
        195                 200                 205

Ile Arg Ile Gly Ser Asp Arg Ile Thr Val Lys Asp Val Ile Asp Arg
    210                 215                 220

Tyr Ser Lys Asp His Asn Val Glu Leu Lys Val Val Ser Glu Gln Ser
225                 230                 235                 240

Ala Glu Asp Ala Lys Lys Glu Phe Thr Glu Ser Leu Lys Ala Gly Phe
                245                 250                 255

Asp Gly Glu Lys Phe Leu Trp Tyr Leu Gln Val Ile Ala Ala Gln Gly
            260                 265                 270

Leu Asp Lys Gly Leu Leu Ser Ser Lys Leu Asp Asn Glu Leu Val Asn
        275                 280                 285

Pro Gly Glu Ser Leu Trp Lys Trp Gly Lys Tyr
    290                 295

<210> SEQ ID NO 7
<211> LENGTH: 166
<212> TYPE: PRT
<213> ORGANISM: Candida albicans

<400> SEQUENCE: 7

Met Ala Ser Ser Val Lys Leu Ala Thr Ala Leu Lys Gln Arg Ala Ile
 1               5                  10                  15

Leu Thr Lys Glu Leu Ser Glu Leu Asp Asp Lys Ile Gln Ser Ser Leu
                20                  25                  30

Ile Ser Gln Val Gly Met Lys Lys Ile Asn Asp Pro Asp Lys Leu Tyr
            35                  40                  45

Leu Asp Tyr Val Ala Lys Ser Gln Glu Leu Ala Lys Leu Val Ser Ser
        50                  55                  60
```

```
Ile Asn Tyr Thr Asn Asn Ile Thr Pro Ile Glu Leu Asp Leu Thr Met
 65                  70                  75                  80

Gly Lys Tyr Asp Asn Thr Ile Lys Thr Ile Asn Asp Ala Leu Ile Cys
                 85                  90                  95

Arg Asp Arg Ile Phe Lys Lys Leu Gln Phe Val Lys Lys Ile Ser Thr
            100                 105                 110

Ala Gly Lys Glu Gln Pro Leu Asp Ser Lys Asp Glu Ile Lys Phe Val
        115                 120                 125

Ser Phe Ile Asp Val Asp Lys Tyr Asp Thr Leu Ala Gln Glu Leu Asn
    130                 135                 140

Thr Gln Phe Glu Asn Leu Asn Leu Lys Leu Gln Glu Ile Asn Trp Gln
145                 150                 155                 160

Val Asp Leu Val Glu Ile
                165

<210> SEQ ID NO 8
<211> LENGTH: 161
<212> TYPE: PRT
<213> ORGANISM: Candida albicans

<400> SEQUENCE: 8

Met Lys Leu Ala Glu Ala Leu Asn Leu Lys Lys Asn Leu Glu Arg Asp
  1               5                  10                  15

Ala Gly Glu Leu Lys Ser Leu Ile Leu Lys Cys Cys Gln Ala Gln Thr
                 20                  25                  30

Gly Glu Asn Pro Pro Phe Asp Pro Asn Glu Leu Phe Glu Gln Tyr Glu
             35                  40                  45

Glu Ile Asp Lys Leu Ile Thr Asp Ile Thr Lys Ile Gln Arg Thr
     50                  55                  60

Asn Asn Glu Ile Lys Phe Ala Tyr Asp Asn Asp Lys Ser Asn Glu
 65                  70                  75                  80

Glu Pro Leu Arg Ser Met Thr Gln Ala Ile Ala Asp Ile Asp Leu
                 85                  90                  95

Glu Arg Gln Ile Asn Val Thr Asp Asp Ile Ile His Asn Gly Ile Ile
            100                 105                 110

Thr Lys Ser Tyr Ser Thr Lys Lys Ile Ala Asp Val Ser His Val Asp
        115                 120                 125

Val Val Ala Tyr Asp Lys Thr Arg Lys Lys Met Asn Glu Arg Leu Asp
    130                 135                 140

Lys Leu Lys Leu Arg Ile Gln Ser Ala Asn Trp Glu Phe Asp Leu Ile
145                 150                 155                 160

Asp

<210> SEQ ID NO 9
<211> LENGTH: 6619
<212> TYPE: DNA
<213> ORGANISM: Candida albicans

<400> SEQUENCE: 9
gttgataaga tctctaatga tgatttgtaa ttttgagcgaa ttttttatctc ttgttgggtt      60 tttgtggatg ttgcacataa agctgcaagg acatcaccaa caacaagtag caagtgtggc     120
tagagttaca aatccgtgta tggtagcaca actgatgaca tttgaataga tgtcatacaa     180
caaaatatgg aatagttttg gataataaac agcacgtgac tattgttaac cagatggctg     240
ttgagaagac actaagacag tacaacagat atctacaaac acctataggt aaatgaggac     300
```

-continued

```
tgcctatttc cttgaaacca ttttctatta cttatttaca ttagttgtat cttttcatta       360
attcaatttc attcataaat atcaaatacc tagtatctaa ctacatattg cctactttaa       420
atgaaaataa accttgggac ataataaatt atatctgata atcttagtac ttgccccatt      480
tccataaaga ttcacctgga ttaaccaatt cattatccaa tttactggag agtaaacctt      540
tatctaaacc ttgagcagca ataacttgta aataccataa gaatttatca ccatcaaaac      600
caactttcaa agattcagta aactctttct tggcgtcttc tgcagattgt tctgaaacaa      660
ttttcaattc aacattatga tctttagagt atctatcaat tacatcttta acagtaattc      720
tatcagaacc aattctaatg gtatctggta attctcttgg attaggatta gtagcaatag      780
aaagtacagc tttaccaaca tcttctaatt tagaaatatc aaattgttga ttaatgtcac      840
caatgagttt aacagttctg tcttcagcat taataccagt tgaaccaacc cattcataaa      900
gaaaagctcc tggaacagca ataacgaag ttataatatc aacaacttta actcctgatt       960
ttctgacatt ttctgaatgt tgagttttaa ttcctaaaaa ccctggagca tattcatcaa     1020
ctttaggaat atcagtacca aattgtgatg ggataaataa ttttggttta attgcatcaa     1080
ctaaattttc gatattggcg aaagcctctg gatttggacc aattaattca ataataacat     1140
cagtaccaga taattttggg ctcaaagttg atttaattga ttcttcattg atttcagaaa     1200
caacatattc aattttgtca ttcttagttt ctggttcctt tctggtaatt gccttgattg     1260
ggaagttgat cttatcatca aaaataccag aattgatagc ttcaagaact ggtttaccta     1320
agaaaccatt caaaccgatg atagtaattg agactttaga cattgtgata gatagatatt     1380
atagattaat tattagataa gcttgtgtaa ttgatcaatt gcttgattaa tgagattgga     1440
aaacaaaaaa ttacaagcca tgttaatgg aggaaacacg tctatttata atgggtttga     1500
ttcaatgtga tgcttaatag gggagtgggg ggttatgcaa tgtaaggaga gacgacaaaa     1560
catacttagc taaaaacaca aacacacatt gttgccatag ttaaatgtgg aattaaatgg     1620
aacaatcttt tcccgtaaaa tgtaaagaaa ggaggaaaaa catacaccaa gaaattgtgg     1680
cgtaatctga aattctttgt ttctctcttt ctctgtttaa tttgtaatca atattttttc     1740
tcattacata atatgcaagt gatgattaat aatcaatatt tgtttatcag ttatatctat     1800
ttaatccttg tatttataat ttcataacaa atcaataaca acaccegcta cagccacatc     1860 acaatcaatt tactggtaac ttatttgtaa tctacatatt acctaagatt gtacagaaat     1920
tgtttctgct tactaaattg tattggtaat aattctacta tggagtaaat agtgttgcta     1980
ttataattgt ggctagtgta tatactgata tcaattaact cgtattaata atatattagg     2040
tgtagcaagc ttgatatctt tgacacagct gttatttgtc tacgccacat tagatttctt     2100
aaccacaact tgtaaggtag tatagacaac taaaaccccta tacagggctc tcttaatcct     2160
tcctccaatg tctgactact aagtaccatc ataccaccag ggttaggtag atatatagac     2220
tctcttggat gcccttgtcg tctactccta aagaggttta catactcaac tagaaaatac     2280
aagctattaa cgtagttaaa gtattacaca actttgtata gctgactttg caaccctcag     2340
attcgttgaa ttttttttgt aagtaacaat ctgtggtctc tggtaaatag ctcaagcctc     2400
agttattact aatcttatta cttatactgc caattctaaa accatcagca aattcattat     2460
taagcattgg ttttagattt catttggtta gtaaagttgc agatacgata tacataacta     2520
agcatagact ataataatcc gaaactaaaa gttgcaatat tccgatatcc ggtatccttt     2580
ccgttgaatc ttttgtattc taaatattaa tacaaggtat agcttgatta attgttggtt     2640
tatgtagatg acagtacttt acttattggt tgtaaataat ctaaagaagt acagaattta     2700
```

-continued

```
tttcaaaatt ggtatccaaa ctcaaccaaa ataataaatc aaccacccaa attgatatta    2760
tctaaaacta caaataaaga tatacaaatg gtttagccta ctgaaagtat acataatagc    2820
atcagttaac tcctcgtagt tcaaccaact aaaaataacc tttataatgg ttctcatctc    2880
tagttgtatc attctgttcc tcatcctcgt catcttcatc ttcgtttgaa ttatcttcaa    2940
cagtatataa cccaattctt cttcgattat tattattgtt atttgatgat agctgtttat    3000 tcttttttaaa tttcttgaaa ttttttccttc cagcatatct cgattcagta tcatcatcaa    3060
cactcttatt tttgttacgt cgatttctag gattaactaa atcaacaatt tccacaattg    3120
ccaaattttg taaattttca ttaatttcaa attcagattc caaatctaaa tttgatgatt    3180
tattcaattc ttgaactttt aaaactgcat ctactaatga cttttggt gtaaattttg      3240 gaattttaaa tggttttga tcatcattag tagtttcatc tttattctta cgttttgatc     3300
cgattgcagg aatttcttcc tcgtcttctt gttcttcttc ttcattttta attgatggaa    3360
aattggaact agactttttgt gaattggaat ctggtttaga tttccttgct aattgatcag   3420
ttgatgatga taaattcgaa tcacccaaac tattaagtgc atcttcttgg ttgattttac    3480
gactttgcgt atgagaattc aacacttttt gattttgctt tatcgttgaa atttttttaa    3540
tgggatcact taattgtgtt atttcttgag ttattgaatc attatcacca ctggtattaa    3600
ttttctgact atttaattct ggtgatgtgc tttattgtc agtgtccaag attgatactt     3660
taggggatgg atcacgtgta gatggtactg gtgtagttgt agttgttggt gttgtcgtac    3720
ctaaggagaa gaaatgtaat ctatcaactt tttcatattt ccttctcttt ctccctgaag    3780
ggtgccgcca cctcaggtgt ttgtgttgta actgatttat catctgatgc taacatagtt    3840
gttgaggtac gtttcaatta aatcaaataa ttttttgggaa gatctagtat tgagccttct   3900
ttaattgatt gccataattg atcttctgtt agagtttgga aattatgtct attcaaagtt    3960
gttgccattg tagttggaac aattaaaatg aattgattat cacctatttt cgatttcaat    4020
acgtcttctt gttgttgtat taacacttta aaatctataa ttattgtttc caaccaattt    4080
attctctcca atgatactaa tttaacatta tttaatggct ttaatctata acttttcggt    4140
aaatagtgat catccttttt tggtaagtat ttcttataat ctatatccaa aagccaatcc    4200
ttaacactat tatacccatc ctcattatca tgacctaata cttttttgtaa ccattgtgaa   4260 tttaaaattg ggatacccctt aataattgcc aatttgaatt catctttttg ttcttcctcc   4320
ttgatatcgt tattatcact atcataataa taatgagtgg catccattat attatcaacg    4380
atttgaatat caataccatg atcttttatt attgttttgt aatgattttg atcacatttt    4440
tcattcgcac taatatataa tttaaaggga atccattcaa tgaacaatgg agtatcttga    4500
gttattattt gtcctgtttg tttatcaatt tgtggaatag tttcaattttt caatttgaat   4560 tcatttgtga aatcaatttc ttctggttta ctatcttttg ataataattt atatgttttc    4620
ccatttataa tcgttttcgc tcgactacat attctaatga ttaataatgt tttatcacta    4680
cctattgaag aagaagacga tgacgatgat ggtggttggg tattgcctat gttgggtcca    4740
gttattaatt caatcaattc tcttgatact ttaggtgacc agaattttat atcagtatttt   4800 tcatcacgtc ccacggtata aatttgtttct ggtgataaat gtttatattc taatgaattg   4860
ttagttggcc tgggggttaaa taaatatcaa aaatcttcag tttctaacat acctcctctt   4920
ggatcatctt tatgatatgt tatccacata gttaagtgta catttgcttg tcaatgaagt    4980
cttcctaagc gaatttgaac tgaaaaaaaa cctatcgcga tccctttaca actttaacaa    5040
```

```
acgtataata aacaggttgc ataaaacctt ctacaaacca ttcagaatct tactttcata      5100
aatagtgatt tattatgaat cgtttcttta aactagtaat acttgtatca ataatgaatc      5160
cctaagcttt tatgttgtaa ctggattaat atcagagttg taggcgtggt cacgtgacat      5220
agatagaata agagtcgaag ggaacaacat taattagact tgatacttat tgtattaaga      5280
taaatgtgaa tttacaataa caaatggtga atatagttta tcagttcata ctagacgatt      5340
agttgaaatt tatttatgtt tgtttggata atcgtttgtt ataaaatag aaatcgtcat      5400 ttttttttg ctcacttgtc ctgttcattc cattcaaggc tgtaactgta aatgttaaac      5460
taaatttcat ttcatttcat tcaacaaaaa aatatcatac tctatttaac ttcaacaaac      5520
taatctcaag aaccagctta cttccttta taatactaca acaacatata ttatacaact      5580
aatcaaagat gggtattaag aaaatgtttc aaaagaaaga accaaccgaa caagaaattc      5640
gtgaagaatt aagtcgagtt ggcatttcta caagatcaaa taatactcga caagagaagt      5700
ttggtgcatt taaaaattat gctcaagaac gagctaatat gaaaccacaa ttaggaccag      5760
ttggtggtaa tccttatgcc aatattaatc ctgggaccaa caataataat aataatccat      5820
atgccaatga taatgggaat aatagtactg gcaaccccaa caacaacaac ggtggtaacc      5880
cctatggtgg tggtgttact aataataatc cttatggagg ctctggtggt aatggaagag      5940
gatcatcacc tagtccttat gcaccgacta catcaacaac tactagatca tctaatccat      6000
atggaaacaa taatggttct agatcaagtc aaaacacttc tagtccttat gccaaatcaa      6060
ctaacaattc atcatattct aactcaccgt attctggatc aactgtaaat aatggtaatc      6120
gtggcggcca tagcaacaac agcaatagtt ctgctggtgg taaccctta gctgccggtg      6180 gtagaagttc acaatctcaa aattcacgag acaatgtata tacagctcct gccactcgta      6240
catcaactag acaaactcaa ggatatggag gtggtgatac cgattcgact cttgacctta      6300
atgccattcc atcacatcaa atgtttgata ataagaaacc gatcaaaaga aatcaacaaa      6360
gttcacaaca acctgccaat gattataatt tagatttaaa tgatgaatat ggcgaagaag      6420
aagacttgaa tttggatata agtgaagtac ctgaagaaca acaacaaatc aattctgaag      6480
atgaagaagt agaagccatt aaacaagata ttaaatttgt caaacaagaa tcagttcaaa      6540
gtaccagaaa tactcttaga atggcacaag aagctgatgc atcgggtact aatactttag      6600
gaatgttagg atcgcaact                                                  6619
```

<210> SEQ ID NO 10
<211> LENGTH: 7965
<212> TYPE: DNA
<213> ORGANISM: Candida albicans

<400> SEQUENCE: 10

```
tagctaagta tgctttgtcg tctctcctta cactgcttaa ccctccaccc ctctatttgg       60
cttcacattg aatcaaacca ttataaatag acgtgtttcc tccattccac atgacttgta      120
attctttgtt ctccaatctc atcaatcaat tacacaagct tatctaataa ttaatctata      180
atatctatct atcacaatgt ctaaagtctc aattactatc atcggtttga atggtttctt      240
aggtaaacca gttcttgaag ctatcaattc tggtatttttt gacgataaaa tcaatttccc      300
aattaaagct attacaagaa aagaaccgga actaaaaat gacaaaattg aatacgttgt      360
ttctgaaatc aatgaagaat caattaaatc aaccttgagc caaaaattat ccggtactga      420
tgttattatt gaattaattg gtccaaatcc agaggctttc gctaatatcg aaaaattaat      480
tgatgcaatt aaaccaaaat tattcattcc atcacaattt ggtactgata ttcctaaagt      540
```

-continued

```
tgatgaatat gctccagggt ttttaggaat caaaactcaa cattcagaaa atgtcagaaa      600
attaggagtt aaagttgttg atattataac ttcgttattt gctgttccag gagcttttct      660
ttatgaatgg gttggttcaa ctggtatcaa tgctgatgac aaaactgtta aacttattgg      720
tgacattaat caacaatttg atatttctaa attagaagat gttggtaaag ctgtactttc      780
tattgctact aatcctaatc caagagaatt accagatacc attagaattg gttctgatag      840
aattactgtc aaagatgtca ttgatagata ttctaaagat cataatgttg aattgaaagt      900
tgtttctgaa caatctgcag aagatgccaa gaaagagttt actgaatctt gaaagctgg      960 ttttgatggt gagaaattct tatggtattt acaagttatt gctgctcaag gtttagataa     1020
aggtttactc tccagtaaat tggacaacga attggtcaac ccaggtgagt ctttatggaa     1080
atggggcaag tactaagatt atcagatata atttattatg tcccaaggtt tattttcatt     1140
taaagtaggc aatatgtagt tagatactaa gtatttgtta ttaataaatc agattaaatc     1200
aatgaaagga ttacaattaa tgtagatgag gattagaaat tggtttctaa tagagaactg     1260
ttgtactctc ttggtgcctt ctcaacagcc atctggttaa cagtagtcac gtgctgttga     1320
tcatccaaaa ctattccaca ttttgcttta tgaaaaccta ccctaatatt gccaattgtg     1380
ctaccataca cggacttgta attccagcca cactttctta cttgttattg ttgatttcct     1440
tgcagcttta tttgcaacat ccacaaaaac ccaacaagac aaaataaacc tcaaattaca     1500
aatcatcatt aaagatctta tcaacaacat gtccccttt tgataattaa caccttaaat     1560
taacctcttg tggggttgat caaaccttga atttgaaccc taagtcaag taagaacgaa     1620 gttaaagcat ccaagtcttg tgaaaagca acatgtaacg gcattttagt ttcgaaccga     1680
gttaaaaatt ggaagtaaga ataagagaaa ctgcgtgacg gctgtgcggc atattattta     1740
aggcaaattg acgatggcaa aaaaaatctt taattttcc gtcttggtaa ttaaatatcg     1800
cgaaggcatt cctttaaagt aatgccttta tgaatggtca aaatgcccta ttttaaaatg     1860
ccttattact ttctattgcg cttatcatga aatttggcta ttactggcac ggcaacaatt     1920
taatcagagc atctgaaatg tgggtgatta attgcagagg gcggttagat ataattttag     1980
atggattgat ttgcctaatt aggaatttgt aactttataa acctctttat aattttcat      2040 cttttcattt ttttcaaaat aaaatgggtt tttcacagaa gtaaagatat tgttcatgct     2100
tattgtgcta acctgatgta aatctcttta ttttaatttg acttcttctt caaaccgttg     2160
aacacggcac caatgaatga taaaattgat gatatttagt taccagcaag caatgatgac     2220
agtattccca agaagaagag acaatggcta cagcaactgg agtaaaacaa gtagtttagc     2280
tacagatcta accttttgt aacaccccaa ccattctctc ttttttgct atattgaaac      2340 actgattttt cttaaattat ttacccaact cctaatggaa tataacaacg aggtgcttct     2400
acttctccac atttccaaca ataaaacatg aatcaacatc aatattgttg caattaatca     2460
aactcttaac atctccacct ccccactaat gatcgatatt atatcaaaac cattggaaat     2520
ttagtttggg tttcatttga atttcggtca agaaaattaa aagtaaaaaa gaaaaaaaa      2580 atttattatt attattcggt tcgatattgc cgcaaaacca aattccatca tcatttcaca     2640
atataatata aaaagtcttc aatcttacac cttgcaaaaa gtttcaattt tttttataa     2700 aatatttatc tatattctaa ttgttacatt tattctttac ttctaatcaa aacaactata     2760
tatcaatatt atgtttgaag taggtgaaaa atatcctgtt gaaagcagca gtagttcaaa     2820
tgacatagaa tctcgtggtg ttcaacctat aacatccctc aaagacaata aatcaatagg     2880
```

-continued

```
aatgatagag aaagataatg atgatctatc atgtgaacaa tatagtactt gtgatgaagt    2940
caaaagagat ttaaaagcaa gacatgtttc tatgattgcc attggtggta caataggtac    3000
agggttattc atatccactg gttctttact tcacaccact ggtccagtaa tgtcattaat    3060
atcattttta tttgtcacaa ctttagcata ttcagttaca caatcacttg gggaaatgac    3120
aacatatatc cccgtttctg gatcatttgc ccaatttata actcgttggg tttcaaaaag    3180
ttgtggtgct gctaatggtt ggttatattg gttttcatgg gccataacat tcgctttaga    3240
attatcagtt gttggtcaag tcatacaata ttggactgat gctgtaccat tagctggttg    3300
gatttccatt ttttcgtct tattaactac atttaattta ttcccggtga aatattatgg    3360
agaggttgaa ttttggattg cttcaactaa agtaattgct attgttgggt ggctcatata    3420
tgcattttgt atggtttgtg gggctggtaa aactggacca gttgggttcc gttattggcg    3480
gaatggatat gcatggggtg atgggatgat agttctgaat aatggtaaat acgccatttc    3540
tttcattaat ggtcttatca atgctgtttt tactttccaa ggtactgaat tggttgctgt    3600
tactgcgggt gaagcttctc caagagcaat ccgtagtgca attaaaaaag tcatgttcag    3660 aatttttggta ttctatgtct tgtgtatgct tttcattggt cttttggttc cttacaacga    3720
tccaaagctt actcaagatg gtggttttac aagaaactct ccattcctta ttgctatgga    3780
aaattccggt actaaagttt taccacacat tttcaatgca gtgatcgtta caacaattat    3840
ttcagctggt aattccaatg tttattcggg atcacgtatt ctttacgggt tagcccaagc    3900
tggtgtagct cctaaatttt tccttaaaac taacaaaggt ggtgttccat attttgctgt    3960
cttgttcact gcggcatttg gtgcattggg atatttagca tgttcggaag atggtaataa    4020
agctttcact tggttattga atattattgc cactgctgga ttgatcgctt ggggattcat    4080
ttctgtgagt catgtcagat tcatgaatgt tcttagaaaa agaggtttaa gtcgagacat    4140
tttaccttat aaagctttt tcatgccata tagtgcatat tatgccatta ttattatatt    4200
cattgttgtg ttgattcaag gtttcacagt gttttgggac ttcaatgcta gtgatttctt    4260
cactgcctat atatccgtga tattatttgt tgttctttgg attggtttcc acttttctt    4320 ttacgggttt ggtaaagatt cttttaaatg ggaaaacata ttaatcccat ggatgattg    4380 tgatattgat tctggtgtta gagatattaa tgatgctgaa tttgatgtac ctgaacctaa    4440
aaatgtttgg gaaagattct ggttacttat tgcttaatct taatttatat aatttaatac    4500
ttaatggaca tagagctttt cagcgattat aatagaaact gattatactt atttaattta    4560 aatctatttta caaatttctc tgaagagtgg ggcgccggtt atacaaactc aacaacgtaa    4620
taattctgtt taccaactct aaccaacaac aatttaccat caatcaaatg attatcaaca    4680
tcaaataata taacatcatc tggatcctca atttgatttc tgtccaatcc catgtataca    4740
ccaccagctt taatcaatct tctcatttca ccctttgatt taccaacaat atcagctaat    4800
aatgcactca atttgatttc ttcatcaggt gaaggcttat ttcttttaaa caaaatacct    4860 gatctttta aattttctat caatttatca gcgcttacat tatcattaaa tggttgatct    4920
ggagtaggga ataaaaatcc cgtaataaac gccatttcgt caccaacacc aacaccatgg    4980
atcaaatcaa caacttcacg tgctaaaaca cgttgagcaa tacgtaaacc aggatcactg    5040
ttatgtttag gtaataattc accttcaatt acattcaagg gcaataatgt gaacactttt    5100
aataatttgc ccactatatc atctggaaca ttaatgaaat attgatacat ttgataagga    5160
gtggtcaaac tagaatcaat aaatactgca tttccagcgg atttaccaaa tttctcacca    5220
ctagaagtag tcaataatgg aacagtaagt ccataagctt catgtttctt gccatgaaat    5280
```

-continued

```
ttcttcaaac gtgaaattaa atcaatacca gcagtaatat tcccccattg atcatttcct    5340
ccaacttgca tattaacatt ttcatccttg tataaatgcc aaaaatcata agcttgtaga    5400
atctgatagg taaattcatt gaatccaatt ccacccagtt ctaatcttga ttgaatggaa    5460
tcacgtgcta acatcgaact aactctaata tgtctaccat atgtagccaa aaattccaac    5520
atcttcacgt tttcccacca tgaagcatta tttaccgatg tagtatcacc gactttttca    5580
gtcatgggga attgtcttga tttggcatat tctatcccat tactcaaaaa tgtagaaatt    5640
tgtcgttgga ttttcgtcac attatcttca acttcaactt catcaatctt gttacgctct    5700
gttttcctcc cacttggatc tccaacaagt ccagtagcac ctccaacaag tccaacaaca    5760
tcattaccac tcattttgaa atgtaataac accattaatg gtaataaatt acctaaatgt    5820
agtgatgatg ccgtaggatc agcaccacaa tataatttga atttgtgatt agaaccacgt    5880
ttagtcaatt tatataaatt atcatcggtt attgattcaa ttaaatgtcg actttgtaaa    5940
tattctaata atgaattgtc gggattggtt tctggtgtta aatctttggc ttcagtcaat    6000
tcatagatgg taggaatgat agtgactgga tctcttgcaa ttgttgaatt aaatctagca    6060
agccttctaa tcaaaggtat gtttctggta tgtgttttca acatattact tgatgtctgg    6120
ttgaacttct ggttgtcgtt tcttcgattg aatttttttct tgtagcttca ttagcgggct    6180
tatttgctat tcgcggtttta attttttaaag aaagccgcaa attcaaatcc aaatccatct    6240
caagctgaga ttttttcttta atttttttttt ttttcacttt actgatatca ttctaatcat    6300
taaacataca aagctcctaa accaatgaca gatcagatta aggggatgaa acataaccaa    6360
gtaaatggta gtaaaaaaag aaagagaaag agaaataaga acaagaaaaa tgacaacaac    6420
acaccagtag agacttccga accaataccg acacctgttt atgaagatga tatccatcga    6480
caaaataaaa agttcaaatt caatgaggaa ggggaaatgg agaaacctca agagtcacct    6540
gaagaggaac aactagaatt agtggcagat caagggggaac cttgcactga agaacctttta    6600
ccacaacatg aaggtttcga agagattgaa gtaactgacg acatagatga aacagaagaa    6660
ccagagaatc ttccaacaag gactcaacaa gaaaaacatc aacacggtaa gaataaattt    6720
aaacaaagc ttgaattcaa agaaaaacc gttgtatata aagatcaaga tgatgaagac    6780
gatgaggaag aaaataatac tttcaatttt tcacaaaatt cgtttcaact tgcagccacc    6840
gcccaacaat tgttacaaat tagagagaaa ttgcccattt atcatcataa ggataaaatc    6900
attgaatgca ttaataataa tcaagtcact atcgtcattg gtgaaaccgg ttcaggtaaa    6960
tcaacacaaa tccctcaatt tttaatgcca gaaaaacccaa aaatgattgg cgtgacacaa    7020
ccaagaagag ttgccgctgc ttcttttagca gcaagagtaa gtgaagaata tggatgtaaa    7080
ttaggtcaag atgttgggta tcaagttaga ttcactaata tgactaacag acaaacaaaa    7140
ttgaaatatt taactgatgg tatgcttcta cgagaaatca tgcttgatct gaatttgact    7200
aaatattcaa caattatcct agatgaagcg catgaaagaa ctattttgac tgatttaatc    7260
atggggtttt tgaaacaaat tattacttct ggtaaaagaa aagatttgaa aatcgtagtt    7320
atgagtgcta ctttgaatgc cgaattattt agtaatttct tgataatgc tcctattta    7380
tacattgaag gtaaaatgta tccagtttca caattctact tagatgctga atctgaagat    7440
attgtggata ccatgatcag aagtataatt caaatcaatc ttaatgaacc cgagggggat    7500
attctttgct tcttacctgg gcaagaggaa attgataatt gtgttaaaag tttagaacaa    7560
ttagcacctc aactacctag ggaggcacca ttgattgttc ctttacctttt atatgcagct    7620
```

-continued

| | |
|---|---|
| ttatcacctg gccaacaatc taaaatattc gaaaaattac ccaagggaag aagaaaagtg | 7680 |
| attttggcga caaatattgc tgaaacatcc attactgttt ctggtgttaa atatgttata | 7740 |
| gattccggat taaggaaaat taaagtttgg aaacataatt taggactttc tacattattg | 7800 |
| actacccta tttcacaagc ttcagcaaga caaagagccg ggagagcagg tagagaatct | 7860 |
| gaaggtaaag tattcagatt atatcctgaa tctacttata tggcacttcc aaaacaacaa | 7920 |
| gaatctgaaa ttaaaagaaa tgatattatt ttacccagtt ttgac | 7965 |

<210> SEQ ID NO 11
<211> LENGTH: 5158
<212> TYPE: DNA
<213> ORGANISM: Candida albicans

<400> SEQUENCE: 11

| | |
|---|---|
| aataattatc attagtcaat tcaacaacta taggagattt agcagcaatc tcttgagagt | 60 |
| tccttcctcg acatctaaca acaacttgga tatttgacat tgatgataat gctgctatga | 120 |
| gtattaattt aactgaaatc acaagatgaa gaatgaaaac aacaacaaca agagaaaga | 180 |
| gtttggcaac gggagaggaa gagaaagtgt aaacaaaaac aaacaaccat aaaaatttac | 240 |
| accataaaaa aaaattagaa gtcgtgattg aactatatgc aggccactat aagaagatat | 300 |
| taaaactact ctgattgaat gaatgaatga ttatataaat ccctcttttc tctcaactta | 360 |
| tagccttaat caaagaaatc atcgtcatct tcatcatcat cagcagctat attttccta | 420 |
| ttgaaagtta ttttttgtttg ttgcttttgt tgactatctc tacttaatcc atctaatatt | 480 |
| tgcacaatat cttttttcacc aagttttttga tgtatttgac ccattgaata taatttaata | 540 |
| atataatttt ctactgcttg agctctatcg ggtctaacaa tctttacacg acttaatctt | 600 |
| tctctagctt cattagttaa gactcgattt aatatggtta tggtcatatt ctcttgtgcc | 660 |
| agatcttgtg cgccacccga agaagaagaa gatggattgg tactactgcc acctccggca | 720 |
| gcatttcttt gtaattctgc taatcttgct tgtcttatag catttaattc tgcgtcatcc | 780 |
| ataatgtata gttgtgaatg aatgagaag gagtagtatt aaaataatta gtgtggatag | 840 |
| agtagtcagt cagtcagcca agtgaatagg gaagtaagga aaaattttgg tcacatttaa | 900 |
| cacgaacttc ttgatcaaag aagaagaaga agaaatttttt tttctgtcat cacgtgcacg | 960 |
| accttttaaat caattgacaa ttcaaaaatt ttgaacaaca acacaacaca actcattctc | 1020 |
| tctttctctt tctctctctc tctctgtgaa aaaaaaaaaa aaagtaaagg acaataaaga | 1080 |
| aatcaaacaa tcaattaaac aaagttaaaa caggaacttt ttctattcaa gttcaaattg | 1140 |
| aaagagaaag agaaatagaa agaaaaaaaa aatttagttc aaattggaat cttgtcttat | 1200 |
| ttagtttcat ttctatatat cttgtcctca tatactatca acatttagat tgatttgaat | 1260 |
| ccagaatcaa caatttcaac aattcttcag atttttgatat agtgtattct atttgacata | 1320 |
| ctttactact accaatacag tcacataatt acatatataa atatattaag agtgggttt | 1380 |
| cggaacattt tcctcctaga tttaatatag aatcccttc ccctaatttt ttttgcatca | 1440 |
| acatttactt aaaaacttca accccaccaa ctcctaaccc taatatttcc cctttctttt | 1500 |
| tttgcatata agactcccac aatgagttca gataaatcaa atttactaaa aaaatacaag | 1560 |
| attgtctttc ttggtgatca aagtgttggt aaaacatcat taatcaccag atttatgtat | 1620 |
| gatacatttg atgaaactta tgctgccacg attggaattg attttttatc gaaaacaatg | 1680 |
| tatttagaag aaggtaaaac cattagatta caattatggg atactgccgg acaagaaaga | 1740 |
| tttcgatcat taataccttc atatattaga gattctcatg ttgcagtaat atgttatgat | 1800 |

```
ataaccaata aaaaatcatt tgataatctt gataaatgga ttaaagatgt taaattagaa    1860
cgaggtgatg atgtaataat agtattagtc ggtaataaac tggatttagc tagtgataaa    1920
cgacaagtta gtttagatga tgttgaaaat ttacaaatta aaattggtgc taaattttc     1980 attgaaactt caactaaagc aaatcataat gttaaattat tatttaaaaa aattgctcaa    2040
tcattacctg attttaatca agattccaat gataaatcaa atgataataa taataataat    2100
aataataatc aactggaaac tattgatata actattgata atactgcacc aaatcctcaa    2160
ggtaccagca catgttgtta gactagaatc ttagtgtaag aactaataaa aaaacagagc    2220
aatgggtaga taatattcta agtatattaa cagttcatac aacaacaacc cacacacaca    2280
catatatata ctatatatat atatcactta tttaatcaat tagatcaaat tcccaatttg    2340
ccgactgtat acgaagtttt aatttatcta atctctcatt cattttcttt cttgtcttgt    2400
catatgcaac cacgtcaaca tgtgacacat cagcaatctt cttggtcgaa tacagttttg    2460
taataatacc attatgaatt atatcatctg tcacattgat ttgtctttct aaatcatcaa    2520
tatcagcaat agcttgtgtc attgatcgaa gtggttcttc attagactta ttatcattat    2580
cataggcaaa ctttatttca ttattggttc gttgtatttt aatagttata tcagtaatta    2640
atttatcaat ttcttcatat tgttcaaata attcattagg atcaaatgga gggttttcgc    2700
cagtttgagc ttgacaacat ttaagaatta atgatttaag ttcaccagca tctcttttcca   2760 agttcttttt taaatttaat gcttcagcta atttcatctt ctctcacaaa atataatata    2820
actcaattat tggttgtaag attatataga ataaagtata tgaaaatgaa aaaaaaatgg    2880
ggtgagaggt aaatgtatcc gaatttataa ttctgttgat agcggagaaa gtataatttt    2940 tattttttt ttggtagttc ggttgtagtt cctctttgct ttattcccct atgcaccctg     3000
gcatacacaa aagtcaattg attgctttct cttgttaagg cttttggggt tggggttgga    3060
gtaattgtcg ttgttgttgt tgctgttcct gatacagtgg aatagagata tgactaattg    3120
gtattggtat gtttatgttt acacaacaca tatgagtcaa cgaaaaatca attggcttga    3180
tctgacttct cctggaacta aattctataa tttcatcaac aattgtaggc aaatgtagac    3240
aaatgttgtg gtttcgtcta gctcaatata accatcaagg tttgttaagc ctccttcctt    3300 tattatttt gcctcttgaa aggcatttt gatgtaacaa agtgattcta caattgttgc      3360
gagcaaatta ttggcaaaca tcttttgtga aagaatcata accttccatt cgtttgttcg    3420
ttttgttagc tcattggctg atgggttctt tagttgctat gaatactgct gctctgtttt    3480
caaaatcctt ttgttgggaa ggttctaccg attgaggttt aacttgtatt atcgtgtaag    3540
tgtgttcctg actccgaatt tttgtctata aatagaccta gaaaagttca cttttttca     3600 aattttttt tattccctttt tcttttttc taatcctcat taacaaatca tattcaaaca     3660
aatcaatcat tttatgcatt gagtcgtatt aattgttgtt tgttggttat agcttgttgg    3720
ttgattgatt ggttggttgg tagtataaac attttcatta ctctaatggc ctcctcagta    3780
aagttggcta cggcacttaa acaacgtgct atattgacaa agaattgtc tgaattagat      3840 gataaaatac aatcttcatt gattctgcaa gttggtatga aaaaaatcaa tgatccagat    3900
aaattgtatt tagattatgt tgctaaatct caagaattgg ctaaattggt atcatcaata    3960
aattatacta ataatataac tccaattgaa cttgatttga caatgggaaa gtatgataat    4020
actataaaaa caattaatga tgcattaatt tgtcgagacc gaatatttaa aaaattacaa    4080
tttgtgaaaa aaatatcaac agcaggtaaa gaacaaccat tagattccaa agatgaaatt    4140
```

-continued

```
aaatttgtat catttattga tgttgataaa tatgatactt tggcccaaga attaaatact     4200
caatttgaga atttgaattt gaaattacaa gaaataaatt ggcaagttga tcttgttgag     4260
atataaaaag gatagtggtg ctggatcgcc attgataata ttctttactt gttactttat     4320
gtaaaaggat ttaaaaaata ttgttggtac tactcgtttc ctccctccca aatcgaataa     4380
tagaactata gaaccatatc cccctataa ttattttatc tgattttatt agttataaag      4440
tacaaatcta ttatcaattg ttttattatt tagtattttc ctccaaagtt ttgaactttt     4500
gttttttatg gttctagttc tttattcttg tttttgggga tttaggggttg ccgcttgatt    4560 tgttgaactt taattgatgc tttgtttagg catagtaatc aagaaaagga agataatgaa     4620
agggtaggga atgagtagga gggcgggttc ggggacaata tacatgtata gttacgtaca    4680
ttaatgtaaa tatattctta aaattcctag tttgtaaatt aattgatggt gttgttgtct    4740
ttgtattttt aaagtattca aaaattttga gtcaatttcg ttaccaaatc ttaatgaata    4800
gtaacacgtc taaccaaatt tcaacaaaaa gtttcatacg accaacaact tatatgcttt    4860
tcagtatgta tatatcttcc atattttat ttgtatatga ttgaattgat aattgtaata     4920
gagttaaaag aatgaagaag aagaagaagt gggttttttgc aaccaacaga acagttaggt   4980
tattcttgtg tacacgacca gatcaaatat gtatgtgaga gagagacgga aatagaattt    5040
tctggaaaga aaaaaaaaaa aaatttcct tcctgttttt ctctcgcccc gtgtgggtgg     5100
gtctctctca ctgttgtgta attcgtacca acaattccgg agccaaattt ctttcacc      5158

<210> SEQ ID NO 12
<211> LENGTH: 968
<212> TYPE: DNA
<213> ORGANISM: Candida albicans

<400> SEQUENCE: 12
cttctctcac aaaatataat ataactcaat tattggttgt aagattatat agaataaagt       60
atatgaaaat gaaaaaaaaa tggggtgaga ggtaaatgta tccgaattta taattctgtt      120
gatagcggag aaaagtataa ttttattttt tttttggtag ttcggttgta gttcctcttt      180
gctttattcc cctatgcacc ctggcataca caaaagtcaa ttgattgctt tctcttgtta      240
aggcttttgg ggttggggtt ggagtaattg tcgttgttgt tgttgctgtt cctgatacag      300 tgaatagag atatgactaa ttggtattgg tatgtttatg tttacacaac acatatgagt       360
caacgaaaaa tcaattggct tgatctgact tctcctggaa ctaaattcta taatttcatc      420
aacaattgta ggcaaatgta gacaaatgtt gtggtttcgt ctagctcaat ataaccatca     480
aggtttgtta agcctccttc ctttattatt tttgcctctt gaaaggcatt tttgatgtaa     540
caaagtgatt ctacaattgt tgcgagcaaa ttattggcaa acatcttttg tgaaagaatc     600
ataaccttcc attcgtttgt tcgttttgtt agctcattgg ctgatgggtt ctttagttgc     660
tatgaatact gctgctctgt tttcaaaatc cttttgttgg gaaggttcta ccgattgagg    720
tttaacttgt attatcgtgt aagtgtgttc ctgactccga attttgtct ataaatagac      780 ctagaaaagt tcactttttt tcaaattttt ttttattccc ttttctttt ttctaatcct      840 cattaacaaa tcatattcaa acaaatcaat cattttatgc attgagtcgt attaattgtt    900
gtttgttggt tatagcttgt tggttgattg attggttggt tggtagtata aacattttca    960
ttactcta                                                              968

<210> SEQ ID NO 13
<211> LENGTH: 456
```

```
<212> TYPE: DNA
<213> ORGANISM: Candida albicans

<400> SEQUENCE: 13
atgtccgacg aaagaacttt tattgctatc aaaccagacg gtgttcaaag aggtttaatc    60
tcatctatct tgggtagatt tgaacaaaga ggtttcaaat tagttggtat taaattggtt   120
caaccaactg aatctttatt gagaactcat tatgaagatt tacaatctaa accatttttc   180
ccatctttat tatcttatat gttatccggt ccagtcttag ctactgtttg ggaaggtaaa   240
gatgttgtta aacaaggtag agccattttg ggtgctacta acccattaca atctgctcca   300
ggtaccatca gaggtgattt tgccattgat atgggtagaa acgtttgtca tggttctgat   360
tctgttgaat ctgctaacaa agaaattgac ttgtggttca agaaagaaga attggttgaa   420
tataaaccag ctttgttcgg ttggatctac gaataa                             456
```

<210> SEQ ID NO 14
<211> LENGTH: 151
<212> TYPE: PRT
<213> ORGANISM: Candida albicans

<400> SEQUENCE: 14

```
Met Ser Asp Glu Arg Thr Phe Ile Ala Ile Lys Pro Asp Gly Val Gln
  1               5                  10                  15

Arg Gly Leu Ile Ser Ser Ile Leu Gly Arg Phe Glu Gln Arg Gly Phe
             20                  25                  30

Lys Leu Val Gly Ile Lys Leu Val Gln Pro Thr Glu Ser Leu Leu Arg
         35                  40                  45

Thr His Tyr Glu Asp Leu Gln Ser Lys Pro Phe Phe Pro Ser Leu Leu
     50                  55                  60

Ser Tyr Met Leu Ser Gly Pro Val Leu Ala Thr Val Trp Glu Gly Lys
 65                  70                  75                  80

Asp Val Val Lys Gln Gly Arg Ala Ile Leu Gly Ala Thr Asn Pro Leu
                 85                  90                  95

Gln Ser Ala Pro Gly Thr Ile Arg Gly Asp Phe Ala Ile Asp Met Gly
            100                 105                 110

Arg Asn Val Cys His Gly Ser Asp Ser Val Glu Ser Ala Asn Lys Glu
        115                 120                 125

Ile Asp Leu Trp Phe Lys Lys Glu Glu Leu Val Glu Tyr Lys Pro Ala
    130                 135                 140

Leu Phe Gly Trp Ile Tyr Glu
145                 150
```

<210> SEQ ID NO 15
<211> LENGTH: 486
<212> TYPE: DNA
<213> ORGANISM: Candida albicans

<400> SEQUENCE: 15

```
atgtctcaat ttacgaatt agctccaaaa gacgccaaag gtgaaccata cccatttgaa     60
caattgaaag ggaaagttgt ccttatcgtc aatgttgctt ccaaatgtgg attcactcct   120
caatacaagg gtttagaaga attgaataag aaatttgctg atcaaccagt acaaatcttg   180
ggtttcccat gtaatcaatt tggccaccaa gaaccaggta gtaacgaaga attggatca   240
ttctgttcat tgaactacgg tgttacattc ccagtcttgg ataaaattga agtcaatggt   300
gacaataccg atccagttta taatatttg aaatcacaaa agagtggtgt tttgggattg   360
```

| accagaatta aatggaattt tgaaaaattc ttgattgacc aaaatggtaa agttattgaa | 420 |
| agattcagtt cattgactag tccagaaagt atcggtacca agattgaaga attgttgaag | 480 |
| aaataa | 486 |

<210> SEQ ID NO 16
<211> LENGTH: 161
<212> TYPE: PRT
<213> ORGANISM: Candida albicans

<400> SEQUENCE: 16

```
Met Ser Gln Phe Tyr Glu Leu Ala Pro Lys Asp Ala Lys Gly Glu Pro
  1               5                  10                  15
Tyr Pro Phe Glu Gln Leu Lys Gly Lys Val Val Leu Ile Val Asn Val
                 20                  25                  30
Ala Ser Lys Cys Gly Phe Thr Pro Gln Tyr Lys Gly Leu Glu Glu Leu
             35                  40                  45
Asn Lys Lys Phe Ala Asp Gln Pro Val Gln Ile Leu Gly Phe Pro Cys
         50                  55                  60
Asn Gln Phe Gly His Gln Glu Pro Gly Ser Asn Glu Glu Ile Gly Ser
 65                  70                  75                  80
Phe Cys Ser Leu Asn Tyr Gly Val Thr Phe Pro Val Leu Asp Lys Ile
                 85                  90                  95
Glu Val Asn Gly Asp Asn Thr Asp Pro Val Tyr Lys Tyr Leu Lys Ser
            100                 105                 110
Gln Lys Ser Gly Val Leu Gly Leu Thr Arg Ile Lys Trp Asn Phe Glu
        115                 120                 125
Lys Phe Leu Ile Asp Gln Asn Gly Lys Val Ile Glu Arg Phe Ser Ser
    130                 135                 140
Leu Thr Ser Pro Glu Ser Ile Gly Thr Lys Ile Glu Glu Leu Leu Lys
145                 150                 155                 160
Lys
```

<210> SEQ ID NO 17
<211> LENGTH: 1080
<212> TYPE: DNA
<213> ORGANISM: Candida albicans

<400> SEQUENCE: 17

| atggctcctc cagcagtttt aagtaaatcc ggtgttatct acggtaaaga cgtcaaagac | 60 |
| ttgtttgact atgctcaaga aaaaggtttt gccattccag ctatcaatgt cacttcatcc | 120 |
| tcaactgttg ttgctgcttt agaagctgcc agagacaaca aggctccaat catcttgcaa | 180 |
| acttctcaag gtggtgctgc ctactttgcc ggtaaaggtg tcgacaacaa agatcaagct | 240 |
| gcttccattg ctggttcaat tgctgccgct cactacatta gagccattgc tccaacttat | 300 |
| ggtatcccag ttgttttaca cactgatcac tgtgccaaaa aattattgcc atggtttgat | 360 |
| ggtatgttga agccgatga agaattcttt gctaagaccg gtactccatt gttctcatcc | 420 |
| cacatgttgg atttatctga agaaccgat gacgaaaaca ttgctacttg tgccaaatat | 480 |
| ttcgaaagaa tggctaaaat gggtcaatgg ttagaaatgg aaattggtat cactggtggt | 540 |
| gaagaagatg gtgtcaacaa cgaacacgtt gaaaagatg ctttatacac ttctccagaa | 600 |
| actgttttcg ctgtctacga atctttacac aagatttctc caaacttttc tattgctgct | 660 |
| gcttttggta acgtccacgg tgtttacaaa ccagtaatg tgcaattgag accagaaatc | 720 |
| ttgggtgacc accaagttta cgctaagaaa caaattggta ctgatgctaa acacccatta | 780 |

```
tacttggttt tccacggtgg ttctggttct actcaagaag aattcaacac tgctatcaag    840
aatggtgttg tcaaggtcaa cttggacact gattgtcaat acgcttactt gactggtatc    900
agagattacg tcaccaacaa gattgaatac ttgaaagcac cagttggtaa cccagaaggt    960
gctgacaaac caaacaagaa atactttgac ccaagagtct gggttagaga aggtgaaaag   1020
accatgtcca agagaattgc tgaagctttg gatattttcc acaccaaagg acaattgtaa   1080
```

<210> SEQ ID NO 18
<211> LENGTH: 359
<212> TYPE: PRT
<213> ORGANISM: Candida albicans

<400> SEQUENCE: 18

```
Met Ala Pro Pro Ala Val Leu Ser Lys Ser Gly Val Ile Tyr Gly Lys
  1               5                  10                  15

Asp Val Lys Asp Leu Phe Asp Tyr Ala Gln Glu Lys Gly Phe Ala Ile
             20                  25                  30

Pro Ala Ile Asn Val Thr Ser Ser Thr Val Val Ala Ala Leu Glu
         35                  40                  45

Ala Ala Arg Asp Asn Lys Ala Pro Ile Ile Leu Gln Thr Ser Gln Gly
 50                  55                  60

Gly Ala Ala Tyr Phe Ala Gly Lys Gly Val Asp Asn Lys Asp Gln Ala
 65                  70                  75                  80

Ala Ser Ile Ala Gly Ser Ile Ala Ala His Tyr Ile Arg Ala Ile
             85                  90                  95

Ala Pro Thr Tyr Gly Ile Pro Val Val Leu His Thr Asp His Cys Ala
            100                 105                 110

Lys Lys Leu Leu Pro Trp Phe Asp Gly Met Leu Lys Ala Asp Glu Glu
            115                 120                 125

Phe Phe Ala Lys Thr Gly Thr Pro Leu Phe Ser Ser His Met Leu Asp
        130                 135                 140

Leu Ser Glu Glu Thr Asp Asp Glu Asn Ile Ala Thr Cys Ala Lys Tyr
145                 150                 155                 160

Phe Glu Arg Met Ala Lys Met Gly Gln Trp Leu Glu Met Glu Ile Gly
                165                 170                 175

Ile Thr Gly Gly Glu Glu Asp Gly Val Asn Asn Glu His Val Glu Lys
            180                 185                 190

Asp Ala Leu Tyr Thr Ser Pro Glu Thr Val Phe Ala Val Tyr Glu Ser
        195                 200                 205

Leu His Lys Ile Ser Pro Asn Phe Ser Ile Ala Ala Ala Phe Gly Asn
    210                 215                 220

Val His Gly Val Tyr Lys Pro Gly Asn Val Gln Leu Arg Pro Glu Ile
225                 230                 235                 240

Leu Gly Asp His Gln Val Tyr Ala Lys Lys Gln Ile Gly Thr Asp Ala
                245                 250                 255

Lys His Pro Leu Tyr Leu Val Phe His Gly Gly Ser Gly Ser Thr Gln
            260                 265                 270

Glu Glu Phe Asn Thr Ala Ile Lys Asn Gly Val Val Lys Val Asn Leu
        275                 280                 285

Asp Thr Asp Cys Gln Tyr Ala Tyr Leu Thr Gly Ile Arg Asp Tyr Val
    290                 295                 300

Thr Asn Lys Ile Glu Tyr Leu Lys Ala Pro Val Gly Asn Pro Glu Gly
305                 310                 315                 320
```

-continued

```
Ala Asp Lys Pro Asn Lys Lys Tyr Phe Asp Pro Arg Val Trp Val Arg
            325                 330                 335

Glu Gly Glu Lys Thr Met Ser Lys Arg Ile Ala Glu Ala Leu Asp Ile
            340                 345                 350

Phe His Thr Lys Gly Gln Leu
            355
```